US009732200B2

(12) United States Patent
Angel et al.

(10) Patent No.: US 9,732,200 B2
(45) Date of Patent: *Aug. 15, 2017

(54) AQUEOUS POLYMER DISPERSION BASED ON N,N-DIETHYLAMINOETHYL METHACRYLATE, ITS PREPARATION AND USE

(71) Applicant: BASF SE, Ludwigshafen (DE)

(72) Inventors: Maximilian Angel, Schifferstadt (DE); Karl Kolter, Limburgerhof (DE); Hartwig Voβ, Frankenthal (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/444,305

(22) Filed: Jul. 28, 2014

(65) Prior Publication Data

US 2014/0335182 A1 Nov. 13, 2014

Related U.S. Application Data

(62) Division of application No. 12/671,529, filed as application No. PCT/EP2008/060154 on Aug. 1, 2008, now Pat. No. 8,790,693.

(30) Foreign Application Priority Data

Aug. 2, 2007 (EP) ..................................... 07113737

(51) Int. Cl.
| | | |
|---|---|---|
| *C08K 3/20* | (2006.01) | |
| *A61K 9/20* | (2006.01) | |
| *A61K 9/28* | (2006.01) | |
| *C08F 2/22* | (2006.01) | |
| *C08F 220/14* | (2006.01) | |
| *C08F 220/34* | (2006.01) | |
| *C09D 133/14* | (2006.01) | |
| *C09J 133/14* | (2006.01) | |
| *A61K 9/16* | (2006.01) | |
| *A61K 9/50* | (2006.01) | |
| *A61K 47/32* | (2006.01) | |
| *A23L 33/10* | (2016.01) | |

(52) U.S. Cl.
CPC ............... *C08K 3/20* (2013.01); *A23L 33/10* (2016.08); *A61K 9/1635* (2013.01); *A61K 9/2018* (2013.01); *A61K 9/2027* (2013.01); *A61K 9/2054* (2013.01); *A61K 9/2846* (2013.01); *A61K 9/2853* (2013.01); *A61K 9/5026* (2013.01); *A61K 47/32* (2013.01); *C08F 2/22* (2013.01); *C08F 220/14* (2013.01); *C08F 220/34* (2013.01); *C09D 133/14* (2013.01); *C09J 133/14* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,853,594 A | 12/1974 | Moroff et al. | |
| 4,112,215 A | 9/1978 | Boessler et al. | |
| 4,181,708 A | 1/1980 | Dannelly | |
| 4,181,710 A | 1/1980 | Dannelly et al. | |
| 4,378,445 A | 3/1983 | Brasen et al. | |
| 4,452,862 A | 6/1984 | Markert et al. | |
| 4,705,695 A | 11/1987 | Lehmann et al. | |
| 4,996,004 A | 2/1991 | Bucheler et al. | |
| 6,624,210 B1 | 9/2003 | Petereit et al. | |
| 7,160,558 B2 | 1/2007 | Petereit et al. | |
| 7,175,857 B2 | 2/2007 | Petereit et al. | |
| 2002/0165315 A1* | 11/2002 | Angel ....................... | C08F 2/22 524/819 |
| 2004/0241130 A1* | 12/2004 | Tamareselvy ............ | A61K 8/04 424/70.16 |
| 2006/0122322 A1* | 6/2006 | Chrisstoffels ........ | A61K 8/0212 524/804 |
| 2008/0262104 A1 | 10/2008 | Angel et al. | |

FOREIGN PATENT DOCUMENTS

| | | |
|---|---|---|
| DE | 1090381 B | 10/1960 |
| DE | 1219175 B | 6/1966 |
| DE | 2135073 A1 | 2/1973 |
| DE | 2512238 B1 | 5/1976 |
| DE | 2838278 A1 | 3/1979 |
| DE | 3049179 A1 | 7/1982 |
| DE | 3426587 | 1/1986 |
| EP | 0058765 A2 | 9/1982 |
| EP | 0101007 A2 | 2/1984 |
| EP | 0172579 A2 | 2/1986 |
| GB | 1097054 A | 12/1967 |
| GB | 1324087 | 7/1973 |
| GB | 2006009 A | 5/1979 |
| JP | 50161580 | 12/1975 |
| JP | 54-046825 | 4/1979 |
| JP | H04163397 A | 6/1992 |
| WO | WO-0005307 A1 | 2/2000 |
| WO | WO-02067906 A1 | 9/2002 |
| WO | WO-2004019918 A1 | 3/2004 |
| WO | WO-2005055986 A1 | 6/2005 |
| WO | WO-2005056619 A1 | 6/2005 |

OTHER PUBLICATIONS

English Translation of Written Opinion of the International Searching Authority from International Application No. PCT/EP2008/060154 dated Mar. 2, 2010.

* cited by examiner

*Primary Examiner* — David J Blanchard
*Assistant Examiner* — Garen Gotfredson
(74) *Attorney, Agent, or Firm* — Drinker Biddle & Reath LLP

(57) ABSTRACT

The present invention relates to a process for preparing an aqueous polymer dispersion by free-radical emulsion polymerization of a monomer mixture which comprises N,N-diethylaminoethyl methacrylate, to the polymer dispersion obtainable by this process, and to the use thereof.

13 Claims, No Drawings

AQUEOUS POLYMER DISPERSION BASED ON N,N-DIETHYLAMINOETHYL METHACRYLATE, ITS PREPARATION AND USE

CROSS-REFERENCE TO RELATED APPLICATIONS

This application is a divisional application of application Ser. No. 12/671,529 filed Feb. 1, 2010. Application Ser. No. 12/671,529 is a national stage application (under 35 U.S.C. §371) of PCT/EP2008/060154, filed Aug. 1, 2008, which claims benefit of European application 07113737.6, filed Aug. 2, 2007.

BACKGROUND OF THE INVENTION

The present invention relates to a process for preparing an aqueous polymer dispersion by free-radical emulsion polymerization of a monomer mixture which comprises N,N-diethylaminoethyl methacrylate, to the polymer dispersion obtainable by this process, and to the use thereof.

DE 1090381 describes a process for coating pharmaceutical forms with coating compositions soluble in the stomach. These comprise a copolymer of 20 to 80% of at least one amino ester of (meth)acrylic acid and 80 to 20% of a monomer which, as homopolymer, forms a water-insoluble polymer. Specific examples mentioned of suitable polymerizable amino esters are the esters of acrylic acid and (meth) acrylic acid with N,N-dimethylaminoethanol, N,N-diethylaminoethanol, N,N-dimethylaminopropanol and N-(hydroxyethyl)morpholine. Suitable comonomers mentioned are lower esters of acrylic acid and preferably of (meth)acrylic acid, such as ethyl acrylate, methyl, butyl and hexyl(meth)acrylates. Preparation takes place by solution polymerization in an organic solvent; no exemplary embodiment is indicated.

DE 1219175 describes a process for preparing veterinary medical active ingredient preparations which are protected from the effect of ruminal fluids of ruminants. For this purpose, these preparations are coated with copolymers which comprise as copolymerized units N,N-dialkylaminoalkyl(meth)acrylamides and a comonomer selected from (meth)acrylates, acrylonitrile and vinyl aromatic compounds. Copolymers based on N,N-dialkylaminoalkyl (meth)acrylates are regarded as disadvantageous according to this document because the ester group is prone to hydrolysis in a basic medium by contrast with the amide group.

DE 2135073 describes coating compositions for pharmaceutical forms which comprise an aqueous polymer dispersion, where the polymer is composed of 10 to 55% by weight of monomers having a carboxyl group and/or a monoalkyl- or dialkylaminoalkyl ester group. Besides a large number of others, diethylaminoethyl methacrylate (DEAEMA) is also mentioned as suitable monomer. Suitable comonomers mentioned are the lower esters of (meth)acrylic acid, preferably methyl methacrylate, (meth)acrylonitrile, vinyl aromatic compounds, vinyl chloride and vinyl acetate. Preparation takes place by aqueous emulsion polymerization, preferably by the emulsion feed process. No specific emulsion polymers based on DEAEMA are disclosed.

DE 2512238 teaches, for providing binders for pharmaceutical coatings with low residual monomer content, the use of a powder obtained by spray drying a polymer dispersion for preparing coating solutions for these pharmaceutical forms. Concerning the dispersions employed for the spray drying, reference is made to DE 1090381, DE 1219175 and DE 2135073.

DE 2838278 describes coatings for oral dosage forms for ruminants composed of
a) at least one film-forming polymer having at least one basic amino group and having a nitrogen content of from 3 to 14%, which is soluble within 24 hours in aqueous ruminal medium at a pH above 5.5, and
b) at least one hydrophobic substance which is dispersed in the polymer and is selected from $C_{12}$-$C_{32}$ fatty acids, Al salts of these fatty acids and/or polycarboxylic acids.

The coating is prepared by employing a solution in an organic solvent. Suitable polymers mentioned are a large number of nitrogen-containing homo- and copolymers, without entering into suitable processes for the preparation thereof. In this connection, a copolymer of 40% N,N-diethylaminoethyl methacrylate is mentioned in exemplary embodiment 29, but without indicating a process for its preparation.

GB 1324087 describes coating polymers for oral dosage forms for ruminants which comprise as copolymerized units
a) at least one N,N-dialkylaminoalkyl(meth)acrylate and
b) at least one ethylenically unsaturated compound selected from vinyl aromatic compounds and derivatives thereof, vinyl esters, esters of (meth)acrylic acid and acrylonitrile.

Disclosed as suitable monomers a) are N,N-dimethylaminoethyl methacrylate (DMAEMA) and tert-butylaminoethyl methacrylate (TBAEMA). Methyl methacrylate is regarded in particular as unsuitable as comonomer b) because it is prone to form coatings which are too brittle. Polymerization processes indicated as suitable are bulk, suspension, solution and emulsion polymerizations. The copolymers of the exemplary embodiments were prepared by solution polymerization.

DE 3426587 A1 describes a process for coating pharmaceutical forms by applying a film of a liquid, film-forming coating agent which comprises a dissolved polymer with tertiary ammonium salt side groups. These polymer solutions can be prepared inter alia by converting copolymers based on N,N-dialkylaminoalkyl(meth)acrylates with aqueous inorganic or organic acids into aqueous ammonium salt solutions.

DE 3049179 A1 is a branched application from DE 2512238 and relates to the use of a powder obtained by spray drying according to the teaching of the latter document, in the form of an aqueous suspension which additionally comprises a plasticizer, for producing coatings by thermal gelation.

EP 0058765 A2 describes coating compositions which are soluble or swellable in gastric fluid for pharmaceutical forms which comprise as binder an emulsion polymer based on N,N-dialkylaminoalkyl(meth)acrylates, there being located between the amino group and the (meth)acrylate group a branched alkylene or aralkylene group having at least three carbon atoms dispersed in a straight chain.

WO 2005/055986 and WO 2005/056619 describe polymers with pH-dependent swelling/dissolving behavior and the use thereof in pharmaceutical forms.

WO 00/05307 is concerned with the provision of coating agents and binders for pharmaceutical forms which comprise (meth)acrylate copolymers which include monomer residues with tertiary amino groups, the intention being that simple dry or aqueous further processing be possible. To this end, this document teaches a process in which (a) a copolymer of $C_1$-$C_4$ esters of (meth)acrylic acid and (meth) acrylate monomers which include tertiary ammonium groups, (b) a plasticizer and (c) an emulsifier with an HLB of at least 14 are blended together, and the coating agent or binder is prepared therefrom by melting, casting, spreading or spraying, where copolymer (a) is introduced in powder form with an average particle size of from 1 to 40 μm. The processability achieved in this case is ascribed to the provision of copolymer (a) in powder form with an extremely small particle size.

WO 02/067906 relates to coating agents and binders with improved water vapor permeability compared with those described in WO 00/05307. In this case, the coating agents and binders are prepared with a mixture which comprises (a) a copolymer of $C_1$-$C_4$ esters of (meth)acrylic acid and further (meth)acrylate monomers having functional tertiary ammonium groups in powder form with an average particle size of from 1 to 40 μm, (b) an emulsifier with an HLB of at least 14 and (c) a $C_1$, —$C_{18}$ monocarboxylic acid or a $C_{12}$-$C_{18}$ hydroxyl compound.

WO 2004/019918 describes coating agents and binders which correspond in terms of their composition to those described in WO 00/05307 and WO 02/067906.

BRIEF SUMMARY OF THE INVENTION

The present invention is based on the object of providing polymers and a process for the preparation thereof which are suitable as coating agents for pharmaceutical dosage forms and can be prepared and/or formulated as easily as possible. It is intended in this connection that the polymers have a range of properties which satisfies as many as possible of the following conditions: coatings for pharmaceutical forms based on films of these polymers should display pH-dependent solubility properties, be distinguished by good barrier properties for water vapor, and/or be suitable for masking active ingredients with unpleasant tastes; preparation should be as easy as possible; elaborate drying and/or other finishing steps during formulation should be avoided as far as possible.

It has now surprisingly been found that polymer dispersions which comprise as copolymerized units N,N-diethyl-aminoethyl methacrylate (DEAEMA) are distinguished by a very good property profile. In particular, dispersions based on this monomer can also be processed in the form of primary dispersions to polymer films, specifically for pharmaceutical dosage forms. It is surprisingly possible in this connection for extremely low-viscosity primary dispersions also to be processed to polymer films.

A first aspect of the invention is therefore a process for preparing an aqueous polymer dispersion Pd) by free-radical emulsion polymerization of a monomer mixture M), comprising
a) N,N-diethylaminoethyl methacrylate, and
b) at least one compound capable of free-radical polymerization selected from esters of α,β-ethylenically unsaturated mono- and dicarboxylic acids with $C_1$-$C_8$ alkanols, in an aqueous medium at a pH of at least 8.

A further aspect of the invention is an aqueous polymer dispersion Pd) obtainable by such a process.

A further aspect of the invention is a coating composition comprising such an aqueous polymer dispersion Pd) or a polymer composition obtainable therefrom by drying.

A further aspect of the invention is a pharmaceutical composition comprising
A) a polymer composition obtainable by drying and/or forming a film of such a polymer dispersion,
B) at least one pharmaceutically acceptable active ingredient, and
C) if appropriate at least one pharmaceutically acceptable excipient.

A specific embodiment is a pharmaceutical composition in the form of an oral dosage form comprising a coating based on such an aqueous polymer dispersion Pd) or a polymer composition obtainable therefrom by drying.

DETAILED DESCRIPTION OF THE INVENTION

The emulsion polymerization takes place according to the invention in an aqueous medium at a pH of at least 8. By this is meant that the pH of the polymerization mixture does not fall below a pH of 8 during the addition of the monomers. After the addition of the monomers, e.g. during any after-polymerization, the pH of the aqueous medium may also assume values lower than 8, but not lower than 7.5. The pH of the aqueous medium throughout the preparation of the polymer dispersion Pd), and also the pH of the resulting polymer dispersion Pd), is preferably at least 8. The pH of the aqueous medium is preferably in a range from 8 to 10, more preferably 8.5 to 9.5. It is advantageous to keep the pH in the aforementioned ranges throughout the polymerization. The pH can be adjusted by adding pH-regulating substances such as bases, acids or buffers to the polymerization mixture. For certain areas of use, however, addition of pH-regulating substances may not be desired. Thus, the use of salts or salt-forming components may lead for example to the films resulting from the dispersions having an undesirably high permeability for active ingredients enclosed therein. This also applies to further salts or salt-forming components such as anionic emulsifiers, long-chain fatty acids etc. In many cases, addition of pH-regulating substances is also unnecessary because the monomer a) employed according to the invention, if appropriate in combination with further cationic monomers c) and, if appropriate, emulsifiers with ionic groups leads to the pH being within the desired range.

Suitable for adjusting the pH during the polymerization or subsequent thereto are in principle all inorganic or organic bases and acids, especially those soluble in water. Examples of suitable bases are alkali metal and alkaline earth metal hydroxides, ammonia and primary, secondary and tertiary amines such as triethylamine, and amino alcohols such as triethanolamine, methyldiethanolamine, dimethylethanolamine or 2-amino-2-methylpropanol. Examples of suitable acids are carboxylic acids such as lactic acid, acetic acid, citric acid or tartaric acid or inorganic acids such as phosphoric acid, diphosphoric acid, sulfuric acid or hydrochloric acid. The pH of the polymerization mixture can be determined before and during the polymerization by suitable measuring devices, for example by a combined electrode.

The polymerization medium used is preferably exclusively water.

In the context of the present invention, the expression alkyl comprises straight-chain and branched alkyl groups. Examples of suitable short-chain alkyl groups are straight-chain or branched $C_1$-$C_8$-alkyl, preferably $C_1$-$C_6$-alkyl and particularly preferably $C_1$-$C_4$-alkyl groups. These include in particular methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-octyl, 3-octyl, 2-ethylhexyl, 1-propylpentyl, etc.

Suitable longer-chain $C_9$-$C_{30}$-alkyl or $C_9$-$C_{30}$-alkenyl groups are straight-chain and branched alkyl or alkenyl groups. Preference is given in this connection to predominantly linear alkyl radicals as also occur in natural or synthetic fatty acids and fatty alcohols, and oxo alcohols, which may additionally be mono-, di- or polyunsaturated if appropriate. These include for example n-nonyl, n-nonenyl, n-decyl, n-decenyl, n-undecyl, n-undecenyl, n-dodecyl, n-dodecenyl, n-tridecyl, n-tridecenyl, n-tetradecyl, n-tetradecenyl, n-pentadecyl, n-pentadecenyl, n-hexadecyl, n-hexadecenyl, n-heptadecyl, n-heptadecenyl, n-octadecyl, n-octadecenyl, n-nonadecyl, n-nonadecenyl etc.

Cycloalkyl is preferably $C_5$-$C_8$-cycloalkyl such as cyclopentyl, cyclohexyl, cycloheptyl or cyclooctyl.

Aryl comprises unsubstituted and substituted aryl groups and is preferably phenyl, tolyl, xylyl, mesityl, naphthyl, fluorenyl, anthracenyl, phenanthrenyl, naphthacenyl and in particular is phenyl, tolyl, xylyl or mesityl.

Compounds which may be derived from acrylic acid and methacrylic acid are in some cases referred to hereinafter in partly abbreviated form by inserting the syllable "(meth)" into the compound derived from acrylic acid.

Monomer A)

N,N-Diethylaminoethyl methacrylate is employed according to the invention as monomer a).

The aqueous polymer dispersion Pd) of the invention is prepared by employing component a) preferably in an amount of from 25 to 65% by weight, particularly preferably 30 to 60% by weight, in particular 38 to 48% by weight, specifically 43 to 47% by weight, based on the total weight of the monomers employed for the polymerization.

Monomer B)

Component b) is selected from esters of α,β-ethylenically unsaturated mono- and dicarboxylic acids with $C_1$-$C_8$-alkanols.

Suitable compounds b) are methyl(meth)acrylate, methyl ethacrylate, ethyl(meth)acrylate, ethyl ethacrylate, n-propyl (meth)acrylate, isopropyl(meth)acrylate, n-butyl(meth)acrylate, sec-butyl(meth)acrylate, tert-butyl(meth)acrylate, tert-butyl ethacrylate, n-hexyl(meth)acrylate, n-heptyl(meth) acrylate, n-octyl(meth)acrylate, 1,1,3,3-tetramethylbutyl (meth)acrylate and ethylhexyl(meth)acrylate.

It is particularly preferred to employ as component b) methyl methacrylate or a monomer mixture comprising methyl methacrylate.

The aqueous polymer dispersions Pd) of the invention are prepared by employing component b) preferably in an amount of from 35 to 75% by weight, particularly preferably 40 to 70% by weight, in particular 52 to 62% by weight, specifically 53 to 57% by weight, based on the total weight of the monomers employed for the polymerization.

Monomer C)

The monomer mixtures M) employed to prepare the polymer dispersions Pd) may additionally comprise at least one further monomer c). The additional monomers c) are preferably selected from esters of α,β-ethylenically unsaturated mono- and dicarboxylic acids with $C_9$-$C_{30}$-alkanols and $C_7$-$C_{30}$-alkanediols, amides of α,β-ethylenically unsaturated mono- and dicarboxylic acids with $C_2$-$C_{30}$-amino alcohols which have a primary or secondary amino group, primary amides of α,β-ethylenically unsaturated monocarboxylic acids and their N-alkyl and N,N-dialkyl derivatives, N-vinyllactams, open-chain N-vinylamide compounds, esters of vinyl alcohol and allyl alcohol with $C_1$-$C_{30}$-monocarboxylic acids, vinyl ethers, vinyl aromatic compounds, vinyl halides, vinylidene halides, $C_2$-$C_8$-monoolefins, unsaturated nitriles, nonaromatic hydrocarbons having at least two conjugated double bonds and mixtures thereof.

Suitable additional monomers c) are esters of α,β-ethylenically unsaturated mono- and dicarboxylic acids with $C_9$-$C_{30}$-alkanols, such as n-nonyl(meth)acrylate, n-decyl (meth)acrylate, n-undecyl(meth)acrylate, tridecyl(meth) acrylate, myristyl(meth)acrylate, pentadecyl(meth)acrylate, palmityl(meth)acrylate, heptadecyl(meth)acrylate, nonadecyl(meth)acrylate, arachinyl(meth)acrylate, behenyl(meth) acrylate, lignoceryl(meth)acrylate, cerotinyl(meth)acrylate, melissinyl(meth)acrylate, palmitoleinyl(meth)acrylate, oleyl (meth)acrylate, linolyl(meth)acrylate, linolenyl(meth)acrylate, stearyl(meth)acrylate, lauryl(meth)acrylate and mixtures thereof.

Further suitable additional monomers c) are esters of α,β-ethylenically unsaturated mono- and dicarboxylic acids with $C_2$-$C_{30}$-alkanediols, such as 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate etc.

Further suitable additional monomers c) are primary amides of α,β-ethylenically unsaturated monocarboxylic acids and their N-alkyl and N,N-dialkyl derivatives, such as acrylamide, methacrylamide, N-methyl(meth)acrylamide, N-ethyl(meth)acrylamide, N-propyl(meth)acrylamide, N-(n-butyl)(meth)acrylamide, N-(tert-butyl)(meth)acrylamide, N-(n-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N-tridecyl(meth)acrylamide, N-myristyl(meth)acrylamide, N-pentadecyl(meth) acrylamide, N-palmityl(meth)acrylamide, N-heptadecyl (meth)acrylamide, N-nonadecyl(meth)acrylamide, N-arachinyl(meth)acrylamide, N-behenyl(meth)acrylamide, N-lignoceryl(meth)acrylamide, N-cerotinyl(meth)acrylamide, N-melissinyl(meth)acrylamide, N-palmitoleinyl(meth) acrylamide, N-oleyl(meth)acrylamide, N-linolyl(meth)acrylamide, N-linolenyl(meth)acrylamide, N-stearylmeth) acrylamide, N-lauryl(meth)acrylamide, N,N-dimethyl (meth)acylamide, N,N-diethyl(meth)acrylamide, morpholinyl(meth)acrylamide.

Further suitable additional monomers c) are N-vinyllactams and their derivatives, which may have for example one or more $C_1$-$C_6$-alkyl substituents such as methyl, ethyl, n-propyl, isopropyl, n-butyl, sec-butyl, tert-butyl etc. These include for example N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. N-Vinylpyrrolidone and N-vinylcaprolactam are preferably employed.

Examples of open-chain N-vinylamide compounds suitable as monomers c) are N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide.

Further suitable additional monomers c) are vinyl acetate, vinyl propionate, vinyl butyrate and mixtures thereof.

Further suitable additional monomers c) are ethylene, propylene, isobutylene, butadiene, styrene, α-methylstyrene, acrylonitrile, methacrylonitrile, vinyl chloride, vinylidene chloride, vinyl fluoride, vinylidene fluoride and mixtures thereof.

The aforementioned additional monomers c) can be employed singly or in the form of any mixtures.

The aqueous polymer dispersions Pd) of the invention are prepared by employing component c) preferably in an amount of from 0 to 80% by weight based on the total weight of the monomers employed for the polymerization. A specific embodiment relates to polymer dispersions Pd) which comprise no additional monomer c) as copolymerized units. When present, component c) is preferably employed in an amount of from 0.1 to 70% by weight, particularly preferably 1 to 60% by weight, in particular 5 to 50% by weight, based on the total weight of the monomers employed for the polymerization.

It is preferred to use no monomer c).

Monomer D)

The monomer mixtures M) employed to prepare the polymer dispersions Pd) may, in addition to compound a), comprise at least one further compound d) which is different therefrom and has an α,β-ethylenically unsaturated double bond capable of free radical polymerization and at least one cationic group per molecule as copolymerized units.

The cationic groups of component d) are preferably nitrogen-containing groups such as primary, secondary and tertiary amino groups, and quaternary ammonium groups. The nitrogen-containing groups are preferably tertiary amino groups or quaternary ammonium groups. Charged cationic groups can be generated from the amine nitrogens either by protonation, e.g. with monobasic or polybasic carboxylic acids, such as lactic acid or tartaric acid, or mineral acids such as phosphoric acid, sulfuric acid and hydrochloric acid, or by quaternization, e.g. with alkylating agents such as $C_1$-$C_4$-alkyl halides or sulfates. Examples of such alkylating agents are ethyl chloride, ethyl bromide, methyl chloride, methyl bromide, dimethyl sulfate and diethyl sulfate.

Examples of suitable compounds d) are the esters differing from DEAEMA of α,β-ethylenically unsaturated mono- and dicarboxylic acids with amino alcohols. Preferred amino alcohols are $C_2$-$C_{12}$-amino alcohols which are $C_1$-$C_8$-mono- or dialkylated on the amine nitrogen. Examples of suitable acid components of these esters are acrylic acid, methacrylic acid, fumaric acid, maleic acid, itaconic acid, crotonic acid, maleic anhydride, monobutyl maleate and mixtures thereof. Acrylic acid, methacrylic acid and mixtures thereof are preferably employed as acid component of these esters.

Suitable additional compounds d) are N,N-dimethylaminomethyl(meth)acrylate, N,N-dimethylaminoethyl(meth)acrylate, N,N-diethylaminoethyl acrylate, N,N-dimethylaminopropyl(meth)acrylate, N,N-diethylaminopropyl(meth)acrylate and N,N-dimethylaminocyclohexyl(meth)acrylate.

Further suitable monomers d) are the amides of the aforementioned α,β-ethylenically unsaturated mono- and dicarboxylic acids with diamines which have at least one primary or secondary amino group. Diamines having one tertiary and one primary or secondary amino group are preferred.

These include N-[2-(dimethylamino)ethyl]acrylamide, N-[2-(dimethylamino)ethyl]-methacrylamide, N-[3-(dimethylamino)propyl]acrylamide, N-[3-(dimethylamino)propyl]-methacrylamide, N-[4-(dimethylamino)butyl]acrylamide, N-[4-(dimethylamino)-butyl]methacrylamide, N-[2-(diethylamino)ethyl]acrylamide, N-[4-(dimethylamino)-cyclohexyl]acrylamide, N-[4-(dimethylamino)cyclohexyl]methacrylamide etc.

Further suitable monomers d) are N,N-diallylamines and N,N-diallyl-N-alkylamines and their acid addition salts and quaternization products. Alkyl in this connection is preferably $C_1$-$C_{24}$-alkyl. N,N-diallyl-N-methylamine and N,N-diallyl-N,N-dimethylammonium compounds such as, for example, the chlorides and bromides are preferred.

Further suitable monomers d) are vinyl- and allyl-substituted nitrogen heterocycles, such as N-vinylimidazole, N-vinyl-2-methylimidazole, vinyl- and allyl-substituted heteroaromatic compounds such as 2- and 4-vinylpyridine, 2- and 4-allylpyridine, and the salts thereof.

The aqueous polymer dispersions Pd) of the invention are prepared by employing component d), when present, preferably in an amount such that the total of the amounts of component a) and of component d) is in a range from 25 to 65% by weight, particularly preferably 30 to 60% by weight, based on the total weight of the monomers employed for the polymerization.

The aqueous polymer dispersions Pd) of the invention are prepared by employing component d) preferably in an amount of from 0 to 50% by weight based on the total weight of the monomers employed for the polymerization.

As already stated, it has surprisingly been found that the polymer dispersions Pd) based on DEAEMA (component a)) according to the invention and employed according to the invention have a particularly good profile of properties. This profile of properties can ordinarily be achieved without employing further monomers having cationic groups. A specific embodiment therefore relates to polymer dispersions Pd) which comprise no additional monomer d) as copolymerized units.

When present, component d) is preferably employed in an amount of from 0.1 to 40% by weight, particularly preferably 1 to 30% by weight, in particular 2 to 25% by weight, based on the total weight of the monomers employed for the polymerization.

In a particularly preferred embodiment of the process of the invention, a monomer mixture M) which consists of
   43 to 47% by weight, based on the total weight of the monomers employed for the polymerization, of N,N-diethylaminoethyl methacrylate a), and
   53 to 57% by weight, based on the total weight of the monomers employed for the polymerization, of at least one compound b), in particular methyl methacrylate,
is employed.

Regulators

The free-radical polymerization of the monomer mixture M) can take place in the presence of at least one regulator. Regulators are preferably employed in an amount of from 0.0005 to 5% by weight, particularly preferably from 0.001 to 2.5% by weight and in particular from 0.01 to 1.5% by weight, based on the total weight of the monomers employed for the polymerization.

Regulators (polymerization regulators) generally refer to compounds with high transfer constants. Regulators speed up chain transfer reactions and thus bring about a reduction in the degree of polymerization of the resulting polymers without influencing the overall reaction rate. It is possible with regulators to distinguish between mono-, bi- or polyfunctional regulators depending on the number of functional groups in the molecule able to lead to one or more chain transfer reactions. Suitable regulators are described for example in detail by K. C. Berger and G. Brandrup in J. Brandrup, E. H. Immergut, Polymer Handbook, $3^{rd}$ edition, John Wiley & Sons, New York, 1989, pages II/81-II/141.

The compounds preferably employed as regulators comprise sulfur in bound form.

Suitable polymerization regulators are moreover thiols (compounds which comprise sulfur in the form of SH groups, also referred to as mercaptans). Preferred regulators are mono-, bi- and polyfunctional mercaptans, mercapto alcohols and/or mercapto carboxylic acids. Examples of these compounds are alkyl thioglycolates, ethylhexyl thioglycolate, cysteine, 2-mercaptoethanol, 3-mercapto-1-propanol, 3-mercaptopropane-1,2-diol, 4-mercapto-1-butanol, mercaptoacetic acid, 3-mercaptopropionic acid, mercaptosuccinic acid, thioglycerol, thioacetic acid, thiourea and alkyl mercaptans such as n-butyl mercaptan, n-hexyl mercaptan, n-dodecyl mercaptan and tert-dodecyl mercaptan.

All said regulators can be employed singly or in combination with one another.

The polymers can be prepared by polymerizing the monomers with the aid of initiators which form free radicals.

Initiators which can be employed for the free-radical polymerization are the peroxo and/or azo compounds customary for this purpose, for example alkali metal or ammonium peroxidisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis-(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azo-bis-isobutyronitrile, azo-bis-(2-amidinopropane)dihydrochloride or 2,2'-azo-bis-(2-methylbutyronitrile). Also suitable are initiator mixtures or redox initiator systems such as, for example, ascorbic acid/iron(II) sulfate/sodium peroxodisulfate, tert-butyl hydroperoxide/sodium disulfite, tert-butyl hydroperoxide/sodium hydroxymethanesulfinate, $H_2O_2/Cu^I$.

The aqueous polymer dispersion Pd) of the invention and used according to the invention is prepared preferably by employing at least one inorganic peroxide as initiator. The initiator is particularly preferably selected from ammonium and alkali metal peroxodisulfates. Sodium peroxodisulfate or potassium peroxodisulfate are very particularly preferred. These peroxodisulfates are preferably employed in the form of an aqueous solution which has a peroxodisulfate concentration in a range from 0.5 to 20% by weight, particularly preferably from 2 to 10% by weight.

The polymerization takes place, as already stated, at an alkaline pH. It is particularly advantageous in this connection not only to keep the polymerization medium in the desired pH range as far as possible throughout the polymerization, but also to adjust the pH of the initiator feed to a pH which is not too acidic. If an aqueous solution of at least one inorganic peroxide is employed as initiator for the polymerization, its pH is preferably greater than 2, particularly preferably greater than 3, in particular greater than 4. Preferred peroxodisulfate concentrations are those mentioned above. Suitable in principle for adjusting the pH are all inorganic or organic bases, especially those which, apart from possible salt formation, do not react with the monomers. Examples of suitable bases are alkali metal and alkaline earth metal hydroxides, tertiary amines such as triethylamine, and amino alcohols such as triethanolamine, methyldiethanolamine or dimethylethanolamine. NaOH or KOH is preferably employed for adjusting the pH. Alternatively, an aqueous sodium peroxodisulfate solution or an aqueous potassium peroxodisulfate solution is employed as initiator for the free-radical emulsion polymerization and is prepared directly before use for the polymerization and thus has a pH in an advantageous range. Prepared directly before use for the polymerization means that preparation takes place not more than 24 hours, preferably not more than 12 hours, in particular not more than 6 hours, before use for the polymerization.

The aqueous polymer dispersion Pd) of the invention and used according to the invention is normally prepared in the presence of at least one surface-active compound.

Suitable surface-active compounds are the protective colloids and emulsifiers normally employed as dispersants in emulsion polymerization, as are described for example in Houben-Weyl, Methoden der organischen Chemie, Volume XIV/1, Makromolekulare Stoffe, Georg-Thieme-Verlag, Stuttgart, 1961, page 411 to 420. Suitable emulsifiers are both anionic and nonionic emulsifiers. The surface-active substances preferably employed are emulsifiers whose relative molecular weights are normally below 2500 g/mol.

Useful nonionic emulsifiers are araliphatic or aliphatic nonionic emulsifiers, for example ethoxylated mono-, di- and trialkylphenols (degree of ethoxylation: 3 to 50, alkyl radical: $C_4$-$C_{10}$), ethoxylates of long-chain alcohols (degree of ethoxylation: 3 to 100, alkyl radical: $C_8$-$C_{36}$) and polyethylene oxide/polypropylene oxide homo- and copolymers. These may comprise the alkylene oxide units randomly distributed or polymerized in the form of blocks. Very suitable examples are EO/PO block copolymers. Ethoxylates of long-chain alkanols (alkyl radicals $C_1$-$C_{30}$, average degree of ethoxylation 5 to 100) and, among these, particularly preferably those with a linear $C_{12}$-$C_{20}$-alkyl radical and an average degree of ethoxylation of from 10 to 50, and ethoxylated monoalkylphenols, are preferably employed.

Particularly preferred nonionic emulsifiers are fatty alcohol alkoxilates of alcohols having 12 to 30 carbon atoms. These preferably have 10 to 30 ethylene oxide units. In a specific embodiment, the nonionic emulsifier is then selected from ethoxilates of cetyl alcohol and/or stearyl alcohol having in each case 10 to 30 ethylene oxide units (such as, for example, 20 ethylene oxide units).

Examples of suitable anionic emulsifiers are alkali metal and ammonium salts of alkyl sulfates (alkyl radical: $C_8$-$C_{22}$), of hemisulfates of ethoxylated alkanols (degree of ethoxylation: 2 to 50, alkyl radical: $C_{12}$-$C_{18}$) and ethoxylated alkylphenols (degree of ethoxylation: 3 to 50, alkyl radical: $C_4$-$C_9$), of alkylsulfonic acids (alkyl radical: $C_{12}$-$C_{18}$) and of alkylarylsulfonic acids (alkyl radical: $C_9$-$C_{18}$). Further suitable emulsifiers are to be found in Houben-Weyl, Methoden der organischen Chemie, Volume XIV/1, Makromolekulare Stoffe, Georg-Thieme-Verlag, Stuttgart, 1961, page 192-208. Suitable anionic emulsifiers are likewise bis(phenylsulfonic acid) ethers and their alkali metal or ammonium salts, having a $C_4$-$C_{24}$-alkyl group on one or both aromatic rings. These compounds are generally known, e.g. from U.S. Pat. No. 4,269,749, and commercially available, for example as Dowfax® 2A1 (Dow Chemical Company).

Particularly suitable anionic emulsifiers are sodiumlaurylsulfate, sodium (cetyl/stearyl)sulfate, etc.

The free-radical emulsion polymerization preferably takes place in the presence of at least one nonionic emulsifier or of an emulsifier mixture which comprises at least one anionic emulsifier and at least one nonionic emulsifier. These include for example mixtures of sodiumlaurylsulfate and the aforementioned fatty alcohol alkoxilates of the alcohols having 12 to 30 carbon atoms and having in each case 10 to 30 ethylene oxide units.

The total amount of emulsifier is generally about 0.05 to 6% by weight, preferably 1 to 5% by weight, based on the amount of monomers to be polymerized. The ratio of anionic emulsifiers to nonionic emulsifiers is preferably in a range from 1:2 to 2:1 and is particularly preferably about 1:1 (such as, for example, 1.3:1 to 1:1.3) by weight. In a specific embodiment, the content of nonionic emulsifiers does not exceed 4% by weight based on the amount of monomers to be polymerized. The emulsifier content of the polymer dispersions Pd) can also be altered after the polymerization. Thus, for example, the emulsifier content can be reduced if the dispersion is subjected to an ultrafiltration. In this case, dispersions with a total emulsifier content of less than 5% by weight, specifically less than 4% by weight, even more specifically less than 3% by weight, based on the amount of monomers, may then result.

The polymer dispersions Pd) can further be prepared by employing dispersants D) different from the aforementioned emulsifiers. These include for example polymeric dispersants which, when present, are generally employed in amounts of from 0 to 10% by weight, preferably 0.01 to 5% by weight, based on the amount of monomers to be polymerized. Preferably, no dispersants different from the aforementioned emulsifiers are employed.

It is further possible to add conventional excipients and additives to the polymer dispersions Pd).

These include for example pH-adjusting substances, reducing agents and bleaches such as, for example, the alkali metal salts of hydroxymethanesulfinic acid (e.g. Rongallit® C from BASF Aktiengesellschaft), complexing agents, deodorants, flavorings, odorants, disinfectants, preservatives and viscosity modifiers such as alcohols, e.g. glycerol, methanol, ethanol, tert-butanol, glycol, propylene glycol, or 2-pyrrolidone, N-methyl-2-pyrrolidone, polyethylene glycol 400 etc.

Suitable preservatives are in principle all substances effective in a pH range above 7. Substances of this type are listed for example in "Praxis der Sterilisation, Desinfektion-Konservierung", Karl Heinz Wallhäußer, 5$^{th}$ revised edition, Georg Thieme Verlag Stuttgart, 1995, pages 465-652. Particularly suitable substances are: benzyl alcohol, 2,4-dichlorobenzyl alcohol, phenylethyl alcohol, 2-phenoxyethanol, 2-phenoxy-1-propanol, chlorphenesin, propylene glycol, formaldehyde, acetaldehyde, acrolein, glyoxal, glutaraldehyde, methyl p-hydroxybenzoate, ethyl p-hydroxybenzoate, propyl p-hydroxybenzoate, butyl p-hydroxybenzoate, benzyl p-hydroxybenzoate, phenol, chlorophenols, quaternary ammonium compounds such as, for example, benzalkonium chloride and cetyl pyridinium chloride, quaternium 15, cresols, chlorocresols, silver and silver salts, organic mercury compounds such as, for example, phenyl mercury acetate, thiomersal, sulfomerthiolate, chlorine, chlorine dioxide, hypochlorites, iodine, hypoiodites, hydrogen peroxide, benzoyl peroxide, 1,3-dimethylol-5,5-dimethylhydantoin, and mixtures thereof.

These excipients and additives can be added to the polymer dispersions in the initial charge, one of the feeds or after completion of the polymerization.

The polymerization generally takes place at temperatures in a range from 0 to 150° C., preferably 20 to 100° C., particularly preferably 55 to 95° C. The polymerization preferably takes place under atmospheric pressure, but polymerization under elevated pressure is also possible, for example the autogenous pressure of the components employed for the polymerization. A preferred pressure range is 1 to 5 bar. In a preferred embodiment, the polymerization takes place in the presence of at least one inert gas such as, for example, nitrogen or argon. The inert gases employed are preferably anhydrous in this connection.

The polymerization takes place in the form of a feed process. The individual feeds can in this connection be introduced into the polymerization zone continuously or in a staged or gradient procedure. In one possible embodiment, the polymerization takes place as a feed process in which part of the polymerization mixture (but preferably without monomers) is initially charged, and the other components are added in whole or in part, batchwise or continuously, together or in separate feeds to the initial charge.

In a preferred embodiment, the components are added to the polymerization reactor from below (immersed).

It is preferred in the process of the invention for no monomer to be initially charged in the polymerization zone employed for the reaction. Furthermore, the free-radical emulsion polymerization preferably does not take place in the presence of a seed latex.

It is preferred for part of the emulsifiers employed and at least part of the aqueous medium to be initially charged in a polymerization zone and heated to a polymerization temperature, and then for the remainder of the polymerization mixture to be introduced via one or more spatially separate feeds into the polymerization zone. The introduction of monomers and/or initiator expediently takes place in this connection at the rate with which they are consumed, i.e. maintaining the polymerization. Normally, polymerization initiator and monomers are added in separate feeds in this case. The monomers can be introduced in principle singly or in the form of mixtures.

The N,N-diethylaminoethyl methacrylate (component a)) is preferably manipulated under essentially anhydrous conditions until it is employed for the polymerization. To this end for example the storage and/or the introduction of component a) into the polymerization zone take place essentially with exclusion with water. The same applies to monomer mixtures which comprise N,N-diethylaminoethyl methacrylate. Suitable processes for discharging, storing and conveying moisture-sensitive substances are known to the skilled worker. These include for example exclusion of water when manipulating component a), as well as previous drying of apparatus surfaces coming into contact with component a). The expression "under essentially anhydrous conditions" means in the context of the invention that contact with small amounts of water, as occurs for example by contact with humidity when being transferred, is usually non-critical.

In a specific embodiment of the process of the invention, the N,N-diethylaminoethyl methacrylate a) is mixed with water in a mixing device directly before use thereof for the polymerization. The expression "directly before use thereof for the polymerization" means in this connection that the mixing with water takes place not more than 1 hour, preferably not more than 10 minutes, particularly preferably not more than 1 minute, before use for the polymerization. The mixing for this purpose also preferably takes place spatially directly before entry into the reaction zone. The N,N-diethylaminoethyl methacrylate a) is preferably mixed in the mixing device with water, at least one emulsifier and, if appropriate, at least one further monomer to obtain a monomer emulsion.

The process of the invention serves to prepare copolymers, where the individual comonomers can in each case be mixed singly or in the form of any mixtures in at least one mixing device to give the emulsion. The comonomers employed for the polymerization are preferably mixed in a mixing device to give the emulsion. A plurality of monomers can be introduced into the mixing device separately or in mixtures which can be generated for example by bringing the individual feeds together in a common pipeline. A hydrous feed to which at least one surface-active substance (emulsifier) has been added before entry into the mixing device is preferably introduced into the mixing device.

The addition of the initiator takes place in a separate feed, generally in aqueous phase, but monomer feed and initiator feed can be combined before entry into the mixing device. Alternatively, the initiator can also be added directly to the reactor independently of the monomer feed.

It is possible if appropriate for further components, which are defined in more detail hereinafter, to be added to the reaction zone, depending on the compatibility together with one of the aforementioned feeds or separately in pure form, as solution in water or else in a suitable solvent.

It is possible to use as mixing device in the process of the invention one or more mixers, it being possible for the mixers to be of the same or different design, and they are used in any sequence, arrangement and combination, such as, for example, arrangement of all the mixers in series, combination of parallel and series arrangement or arrangement of all the mixers in parallel. If a plurality of mixers is used, arrangement in series is preferred. Suitable mixers are dynamic mixers whose mixing elements comprise movable parts, and static mixers, i.e. mixing elements without movable parts in the interior. Mixers which operate in particular according to the inline principle are preferred. Suitable mixers are described for example in A. Echte, Handbuch der technischen Polymerchemie, VCH Verlagsgesellschaft Weinheim, pages 104 et seq. (1993).

In a preferred embodiment of the process of the invention, a mixing device which comprises at least one dynamic mixer is employed.

Suitable dynamic inline mixers are for example the Kratz heat exchangers described in ZFL-Zeitschrift für Lebensmitteltechnologie und-Verfahrenstechnik (1982) 33(3), pages 139 et seq., size-reduction machines operating by the rotor-stator principle, such as, for example, toothed-wheel dispersers (e.g. of the Megatron® type from Kinematica), colloid mills and corundum disc mills, and high-pressure and ultrasonic homogenizers.

Suitable static inline mixers are those described for example in ZFL-Zeitschrift für Lebensmitteltechnologie und-Verfahrenstechnik (1982) 33(3) pages 139 et seq., such as, for example, the Ross ISG mixer in which the fluid flow is guided by internals with perforations which divide it into part streams which are then laterally displaced and brought together again in a different sequence. Also suitable are static mixers which comprise a plurality of identical or different fixed mixing elements which, are for example staggered in each case, are incorporated in succession in a pipe or a channel. These include for example Kenics, Sulzer SMV and Sulzer SMX mixers.

Further suitable static inline mixers are shear mixers like the jet dispersers described in EP-B-101 007.

Further suitable mixers are also devices for inline emulsification such as membranes and jet mixers.

The mixing device used in a suitable embodiment is at least one inline mixer which is expediently mounted directly in front of the reaction vessel.

It is particularly preferred for the mixing device to comprise a dynamic mixer and, if appropriate, a static mixer. If two mixers are used, these are arranged in series. A dynamic mixer preferably used in this connection is a continuous tube mixer or a toothed-wheel disperser.

Reaction zones suitable for the emulsion polymerization are the reactor types usual for this purpose. These include for example stirred vessels. Examples of suitable stirrer types comprise propeller stirrers, impeller stirrers, disc stirrers, paddle stirrers, anchor stirrers, inclined paddle stirrers, crossbeam stirrers, helical ribbon impellers, screw-type stirrers, etc.

Preferably all the parts of the system which come into contact with the aqueous polymer dispersion Pd) are brought into contact with a base before starting the free-radical emulsion polymerization. Suitable for this purpose are aqueous solutions of the bases mentioned at the outset, preferably aqueous NaOH and KOH. Dilute aqueous solutions (e.g. 2 to 4% by weight) are preferably employed. For this purpose, the reactor, including any reactor internals, stirring devices, heating/cooling devices, etc. and all surfaces coming into contact with the reactor discharge are flushed with an aqueous base.

The dispersions resulting in the polymerization can be subjected, following the polymerization process, to a physical or chemical after-treatment. Examples of such processes are the known processes for reducing residual monomers, such as, for example, after-treatment by addition of polymerization initiators or mixtures of a plurality of polymerization initiators at suitable temperatures, after-treatment of the polymer solution with steam or stripping with inert gas or treatment of the reaction mixture with oxidizing or reducing reagents, adsorption processes such as adsorption of impurities on selected media such as, for example, activated carbon or an ultrafiltration. In a preferred embodiment, the resulting polymer dispersion Pd) is subjected to an ultrafiltration. It is thus possible to obtain dispersions with low residual monomer contents as are necessary in particular for pharmaceutical applications. In this connection it is possible by ultrafiltration in particular to obtain dispersions Pd) with a very low content of polymerizable monomers.

To purify the dispersion by ultrafiltration, i.e. to remove low molecular compounds dissolved in the dispersing medium, the dispersion is brought into contact with a membrane under pressure, and polymer-free permeate (filtrate) comprising the dissolved compounds is drawn off on the reverse side of the membrane at a lower pressure than on the feed side. The low molecular weight compounds which can be removed by ultrafiltration are selected from precursors, decomposition products of the precursors, oligomers, salts, surfactants etc., and mixtures thereof. A concentrated polymer dispersion which is depleted in dissolved compounds is obtained as retentate. To prevent the polymer concentration becoming too high, the removed amount of permeate can be continuously or discontinuously replaced in the retentate by dispersant (water). An ultrafiltration which is not carried out to dryness, but in which the removed amount of permeate is replaced is also referred to as diafiltration. It is generally possible for the dispersion to be employed for the ultrafiltration in the concentration in which it results in the synthesis (e.g. 20 to 40% strength in water). It is, of course, likewise possible to dilute the dispersion with water before the ultrafiltration and then to subject it to the ultrafiltration at a lower polymer concentration (preferably to a diafiltration, in which case removed permeate is replaced in the retentate by addition of water so that the polymer concentration remains constant) and if appropriate subsequently to concentrate it to the desired polymer concentration.

It is possible to prevent or minimize deposition (build up of covering layer) of polymer particles on the membrane surface, which leads to a marked reduction in the permeate flow, for example by pump circulation, mechanical movement of the membrane or stirring units between the membranes. In this case there is preferably generation of a relative velocity between membrane and dispersion in the range from 0.1 to 20 m/s (coiled geometry: 0.1 to 5 m/s, tubular geometry: 1 to 6 m/s, rotational geometry: 2 to 20 m/s). The polymer dispersions of the invention surprisingly exhibit a shear stability sufficient for this purpose.

Preferred geometries are, besides tubular membrane geometry with membrane internal diameters of from 1 to 25 mm, preferably 2 to 15 mm, a modular geometry, with which the shear and the transmembrane pressure can be adjusted independently of one another, because greater permeate flows can be achieved in this case than with tubular membranes.

With appropriate modules there is on the one hand generation of a relative velocity between membrane and suspension of between 2 to 20 m/s through mechanical movement of the membrane or by stirring units between the membranes, and on the other hand control of the transmembrane pressure by controlling the amount of feed, retentate or permeate.

The diafiltration and concentration can take place in a batch procedure by passing the suspension several times through the membrane modules or continuously by passing once through one or more feed and bleed stages connected in series.

For the membrane process it is possible to employ membrane separating layers with pore diameters between 1 nm (molecular cut-offs about 1 kD) and preferably 10 nm (molecular cut-offs about 20 kD) to 400 nm (molecular cut-offs about 500 kD). The separating layers may consist of organic polymers, ceramic, metal, carbon or combinations thereof and must be stable in the feed medium at the filtration temperature. For mechanical reasons, the separating layers are usually applied to a mono- or multilayer porous substructure made of the same or else a plurality of different materials as the separating layer. Examples of possible material combinations are detailed in the following table:

| Separating layer | Substructure (coarser than separating layer) |
|---|---|
| Metal | Metal |
| Ceramic | Metal, ceramic or carbon |
| Polymer | Polymer, metal, ceramic or ceramic on metal |
| Carbon | Carbon, metal or ceramic |

Ceramic: e.g. $\alpha$-$Al_2O_3$, $ZrO_2$, $TiO_2$, SiC, mixed ceramic materials
Polymer: e.g. PP, PTFE, PVDF, polysulfone, polyethersulfone, polyetheretherketone, polyamide, polyacrylonitrile, regenerated cellulose Particularly preferred separating layers are composed of hydrophilic materials such as, for example, metal, ceramic, regenerated cellulose, acrylonitrile and hydrophilized acrylonitrile, polysulfone and hydrophilized polysulfone, polyethersulfone and hydrophilized polyethersulfone, polyetheretherketone and hydrophilized polyetheretherketone, and hydrophilized PVDF. Examples have been run with regenerated cellulose (30 kD), hydrophilized PVDF (30 nm) and hydrophilized polyethersulfone (20 kD).

The membranes can be employed in principle in flat, tubular, multichannel element, capillary or coiled geometry for which appropriate pressure housings which allow separation between retentate and the permeate are available.

The optimal transmembrane pressures between retentate and permeate are, substantially dependent on the diameter of the membrane pores, the hydrodynamic conditions which influence the buildup of covering layer, and the mechanical stability of the membrane at the filtration temperature, depending on the type of membrane, preferably in a range from 0.2 to 20 bar, particularly preferably in a range from 0.3 to 6 bar. Higher transmembrane pressures usually lead to higher permeate flows. It is moreover possible in the case where a plurality of modules are arranged in series for the transmembrane pressure to be lowered and thus adapted for each module by raising the permeate pressure. The operating temperature depends on the membrane stability and the thermal stability of the dispersion. A suitable temperature range for ultrafiltration is 20 to 80° C. Higher temperatures usually lead to higher permeate flows. The permeate flows which can be achieved depend greatly on the type of membrane and membrane geometry employed, on the process conditions, on the feed composition (substantially the polymer concentration). The flows are typically in a range from 5 to 500 kg/m²/h. Thus, for example, permeate flows in a range from 15 to 70 kg/m²/h are reached in a rotational system with 30% polymer content, 40° C. and a transmembrane pressure of 1 bar on a regenerated cellulose membrane with a cut-off of 30 kD, depending on the speed of rotation. In this case, the permeate flow typically increases from the start of ultrafiltration to the end by a factor of about 2. The desired depletion of the water-soluble constituents is generally achieved by a diafiltration step with a solvent exchange coefficient of up to 5, preferably of up to 3. In this connection, the solvent exchange coefficient indicates how often the solvent of the dispersion is exchanged during the diafiltration. This means that with a solvent exchange coefficient of X, for each m³ of dispersion X m³ of permeate is removed and, at the same time, X m³ of solvent (water) is introduced into the dispersion.

The following membranes can be employed for example:

| Manufacturer | Membrane | Cut-off (kD) Pore diameter (nm) |
|---|---|---|
| Atech innovations GmbH | UF/$TiO_2$ on $\alpha$-$Al_2O_3$/1, 2 | 20 kD |
| | UF/$ZrO_2$ on $\alpha$-$Al_2O_3$/1, 2 | 50 nm |
| | MF/$\alpha$-$Al_2O_3$ on $\alpha$-$Al_2O_3$/1, 2 | 0.1; 0.2; 0.4 µm |
| Rhodia/Orelis | MF/$ZrO_2$ or $TiO_2$ on ceramic/1, 2 | 0.1; 0.2; 0.45 µm |
| | UF/$ZrO_2$ or $TiO_2$ on ceramic/1, 2 | 15, 50, 150; 300 kD |
| | UF/$ZrO_2$—$TiO_2$ on carbon/1 | 50; 150; 300 kD |
| | MF/$ZrO_2$—$TiO_2$ on carbon/1 | 0.14 µm |
| Pall-Schumacher | UF/$TiO_2$ or $ZrO_2$ on ceramic/1, 2 | 5, 10 and 50 nm |
| | MF/$\alpha$-$Al_2O_3$ on ceramic | 100 and 200 nm |
| Graver Technologies | UF/$TiO_2$ on steel/1 | 100 nm |
| Creavis | UF/$ZrO_2$ on $\alpha$-$Al_2O_3$ and metal/3 | 25, 80 nm |
| Bekaert | MF/metal on metal/1 | 0.2-0.5 µm |
| GKN | MF/metal on metal/1 | 0.3 µm |

-continued

| Manufacturer | Membrane | Cut-off (kD) Pore diameter (nm) |
|---|---|---|
| NADIR Filtrations GmbH | UF/polyethersulfone (hydrophilized)/ 1, 3 | 4-150 kD |
| | UF/PAN/1 | 20, 40 kD |
| | UF/regenerated cellulose/3 | 5, 10, 30, 100 kD |
| Osmonics/Desal | UF/PAN (hydrophilized)/3 | 100 kD |
| X-Flow | UF/PVDF (hydrophilized)/1 | 30 nm |

1: tubular membrane;
2: multichannel element;
3: flat membrane for coiled, bag, stacked plate or special modules with moving membrane or stirring units between the membranes After the polymer dispersions Pd) of the invention have been subjected to an ultrafiltration they are distinguished by very low residual contents of low molecular compounds dissolved in the dispersing medium. This applies in particular to unwanted hydrolysis products from monomers a) and b). It is thus possible to provide dispersions which are suitable in particular as coating compositions for pharmaceutical dosage forms.

The polymer dispersions Pd) of the invention comprise N,N-diethylaminoethanol preferably in an amount not exceeding 2500 ppm by weight, particularly preferably not exceeding 1000 ppm by weight, in particular not exceeding 500 ppm by weight.

The polymer dispersions Pd) of the invention comprise methacrylic acid preferably in an amount not exceeding 100 ppm by weight, particularly preferably not exceeding 50 ppm by weight.

The polymer dispersions Pd) of the invention comprise methanol preferably in an amount not exceeding 500 ppm by weight, particularly preferably not exceeding 250 ppm by weight, in particular not exceeding 50 ppm by weight.

It is possible in principle to add to the polymer dispersions Pd) of the invention at least one of the aforementioned additives or excipients during or after the ultrafiltration. These include for example buffer substances, preservatives or antioxidants.

It is also possible for further processing steps to follow, for example suitable drying processes. The polymer dispersions Pd) can be converted into powder atm by various drying processes such as, for example, spray drying, fluidized spray drying, drum drying or freeze drying. Spray drying is preferably employed. The dry polymer powders obtained in this way can advantageously be converted again into an aqueous dispersion by redispersion in water at a suitable pH. However, the dispersions obtained by the process of the invention are preferably marketed and/or further processed directly as primary dispersion.

The dispersions of the invention surprisingly have excellent physical and chemical stability. Thus, the dispersions do not sediment or coagulate on storage at room temperature for several years. The technical use properties are unchanged after storage. Contrary to all expectation, only a minimal hydrolysis of the ester groups of the polymer takes place, despite an alkaline pH and the presence of amino groups which normally catalyze hydrolysis.

The polymers present in the dispersions Pd) of the invention, preferably have an average molecular weight $M_w$ determined by gel permeation chromatography in the range from 30 000 to 500 000, particularly preferably 60 000 to 140 000, in particular 80 000 to 120 000, g/mol.

The GPC is carried out by the following method:
Eluent: THF+0.02 mol/l triethylamine
Column temperature: 35° C.
Flow rate: 1 ml/min
Injection: 100 µl of a solution with 2 [g/l]
Sample solutions were filtered through Sartorius Minisart SRP 25 (pore width 0.2 [µm]).
Combination of Separating Columns:

| No. | Columns i.d. [mm] | Length [cm] | Separation material | Cut-off |
|---|---|---|---|---|
| 775 | 7.5 | 30 | PL Gel Mixed B | 8 000 000 |
| 776 | 7.5 | 30 | PL Gel Mixed B | 8 000 000 |

Tray number of the combination at the indicated flow rate: 40 000
Detector: HP-1100 differential refractometer
Calibration: The calibration took place with polystyrene standards with a narrow distribution from Polymer Laboratories with molecular weights from M=580 to M=7 500 000, and hexylbenzene (M=162). Elution regions located outside this range were estimated by extrapolation.

The polymers present in the dispersions Pd) of the invention preferably have a K value (determined by the Fikentscher method on a 1% strength solution in N-methylpyrrolidone (NMP)) in the range from 40 to 60.

1% strength solutions for determining K values are prepared by weighing out an amount of sample whose solids content is about 0.7 g and adding the calculated volume of solvent. The proportion of solvent is calculated by the following equation:

$$V_L = \left(\frac{m_s * SC}{c}\right) - m_s$$

The meanings therein are:
$V_L$=calculated solvent volume [ml]
$m_S$=weight of sample [g]
SC=solids content [g/100 g]
c=intended concentration [g/100 ml]
The density of the sample is assumed to be 1 g/ml in this calculation. The total volume is approximately 70 ml. The solution is dissolved at room temperature and filtered through a 0.40 µm metal sieve. A viscosity measurement is then carried out by determining the times for the filtered solutions and pure solvent to run through a capillary viscometer at 25° C. (±0.05° C.).

The glass transition temperature $T_G$ (determined by DSC) is preferably in a range from 40 to 70° C., particularly preferably 52 to 62° C.

The polymers present in the dispersions Pd) of the invention are essentially random copolymers.

The average particle diameter of the polymer particles present in the polymer dispersion Pd) (determined using an analytical ultracentrifuge) is preferably in a range from 70 to 200 nm, particularly preferably from 80 to 150 nm, in particular from 90 to 120 nm. The particle size distribution is preferably essentially unimodal.

The light transmission of the dispersions Pd) of the invention, deter mined on a 0.01% strength dispersion in water (2.5 cm cuvette, white light), is preferably at least 70%, particularly preferably at least 80%. Determination of the light transmission is described for example in Dieter Distler, Wässrige Polymerdispersionen, Wiley-VCH (1999), page 40.

The solids content of the dispersions Pd) of the invention is preferably 10 to 50% by weight, particularly preferably 20 to 40% by weight. When a dispersion is purified by ultrafiltration, the dispersions of the invention preferably have solids content in these ranges before and after the ultrafiltration. It is, of course, likewise possible to subject a dilute polymer dispersion to concentration by ultrafiltration.

The dispersions of the invention exhibit for example even with a solids content of 30% by weight extremely low viscosities, preferably of less than 50 mPas, particularly preferably less than 25 mPas and especially less than 10 mPas (values determined using a Brookfield viscometer at 20° C. and 100 s$^{-1}$). Such low viscosities are of particular importance for many applications.

The charge of the polymers present in the dispersions Pd) of the invention depends on the pH of the dispersion. The isoelectric point is preferably in a pH range from about 7.5 to 8.5. The finished dispersion preferably has a pH in the range from 8 to 10, particularly preferably from 8.5 to 9.5 (with a solids content of 30% by weight). It is advantageous for the pH of the finished dispersion to be chosen to be higher (more alkaline) than its isoelectric point, as long as dissolution or swelling of the polymer particles present in the dispersion is not desired. The dispersions of the invention are therefore preferably basic dispersions.

The polymer dispersions Pd) of the invention are distinguished by their pH-dependent solubility. The pH range in which the dispersion dissolves on acidification is adjusted for example by the amount of N,N-diethylaminoethyl methacrylate (monomer a) in the polymer and, if appropriate, by using further monomers with cationic groups (monomer d). The polymers present in the polymer dispersions Pd) of the invention preferably dissolve at a pH not above 6.8, particularly preferably at a pH not above 5.5.

A further aspect of the invention is therefore an aqueous polymer dispersion Pd) which is soluble through reduction in the pH and comprises
at least one polymer which comprises
  a) N,N-diethylaminoethyl methacrylate, and
  b) at least one compound capable of free radical polymerization and selected from esters of α,β-ethylenically unsaturated mono- and dicarboxylic acids with $C_1$-$C_8$-alkanols,
    as copolymerized units,
at least one emulsifier selected from anionic and nonionic emulsifiers, and
water.

A preferred embodiment comprises polymer dispersions which comprise a polymer which comprises
  43 to 47% by weight, based on the total weight of the monomers employed for the polymerization, of N,N-diethylaminoethyl methacrylate a), and
  53 to 57% by weight, based on the total weight of the monomers employed for the polymerization, of at least one compound b)
as only monomers in the copolymer.

The polymer dispersions Pd) described above are outstandingly suitable for producing pharmaceutical compositions. For the first time, an aqueous dispersion of a basic amino group-containing polymer is provided therewith, which dispersion is suitable for pharmaceutical use, has an appropriate purity and has sufficient stability. They serve moreover for example as polymeric film formers, especially for producing coating compositions for pharmaceutical dosage forms.

The formulation base for coating compositions of the invention for pharmaceutical dosage forms may comprise at least one further pharmaceutically acceptable excipient. Pharmaceutically acceptable excipients are those known to be usable in the area of pharmacy, food technology and adjacent sectors, in particular those listed in relevant pharmacopeias (e.g. Ph. Eur., USP, JP), and other excipients whose properties do not stand in the way of physiological use.

Possibilities for suitable excipients are: flavorings, taste-improving substances, sweeteners (sugars, sugar alcohols, sweeteners such as, for example, aspartame, saccharin-Na, sodium cyclamate), lubricants, wetting agents, mold release agents, plasticizers, non-stick agents, deoxidants, stabilizers, pore formers, neutralizers, gloss agents, colorants, pigments, disinfectants or preservatives, thickeners, etc. Such substances are described for example in Fiedler, H. P. Lexikon der Hilfsstoffe für Pharmazie, Kosmetik and angrenzende Gebiete, 4$^{th}$ edition, Aulendorf: ECV-Editio-Cantor-Verlag, 1996.

Usual amounts of the excipients are in a range from in each case 0 to 50% by weight, preferably 0 to 20% by weight, in particular 0.01 to 10% by weight, based on the total weight of the coating composition.

The coating compositions can be prepared for example by intimate mixing of a polymer dispersion of the invention or of a polymer obtainable therefrom by a drying process with at least one excipient. In a particularly preferred embodiment, the polymer dispersion of the invention is employed as such, without previous drying, for producing a coating composition. However, it is also possible first to subject a polymer dispersion of the invention to a drying and to employ the polymer composition obtained in this way to produce a coating composition. The polymer composition can then be employed for example in powder form, as melt, solution or secondary dispersion for producing the coating composition.

A further aspect of the invention is a coating composition comprising such an aqueous polymer dispersion Pd) or a polymer composition obtainable therefrom by drying.

A further aspect of the invention is a pharmaceutical composition comprising
  A) a polymer composition obtainable by drying and/or forming a film of such a polymer dispersion,
  B) at least one pharmaceutically acceptable active ingredient, and
  C) if appropriate at least one pharmaceutically acceptable excipient.

The polymer dispersions of the invention can be used in the pharmaceutical compositions for example for producing a binder or a coating composition. The functional effect in this case usually arises through drying and/or formation of a film of the coating composition or binder. This drying and/or film formation can take place, irrespective of the application process, by input of energy. This can take place by convection (heat), radiation (infrared or microwaves) or conduction. Water employed as dispersant for the application evaporates during this, and the evaporation can be expedited if appropriate also by use of a vacuum.

The coating compositions of the invention can be used for example in powder form, as melt or in aqueous emulsion by granulation, casting, spreading or by spray application. Use as polymer dispersion is preferred, specifically as primary dispersion. The coating compositions of the invention may additionally comprise at least one further polymer component. It is moreover possible to employ mixtures of at least two dispersions, of at least one dispersion and at least one solution, of at least one dispersion and at least one powder, of at least two powders, etc.

The formulation of the invention is suitable for administering in principle any active pharmaceutical ingredients which can preferably be administered in sealed or protected form, such as antidepressants, beta-receptor blockers, antidiabetics, analgesics, antiinflammatory drugs, antirheumatics, antihypotensives, antihypertensives, psychoactive drugs, tranquilizers, antiemetics, muscle relaxants, glucocorticoids, agents for the treatment of ulcerative colitis or Crohn's disease, antiallergics, antibiotics, antiepileptics, anticoagulants, antimycotics, antitussives, arteriosclerosis remedies, diuretics, enzymes, enzyme inhibitors, gout remedies, hormones and their inhibitors, cardiac glycosides, immunotherapeutics and cytokines, laxatives, lipid-lowering agents, gastrointestinal therapeutics, migraine remedies, mineral products, otologicals, Parkinson remedies, thyroid therapeutics, spasmolytics, platelet aggregation inhibitors, vitamins, cytostatics and metastasis inhibitors, phytopharmaceuticals, chemotherapeutic agents, nutraceuticals, vitamins, carotenoids and amino acids.

Examples of suitable active ingredients are: acarbose, non-steroidal antirheumatics, cardiac glycosides, acetylsalicylic acid, virustatics, aclarubicin, acyclovir, cisplatin, actinomycin, alpha- and beta-sympathomimetics, allopurinol, alosetron, alprostadil, prostaglandins, amantadine, ambroxol, amlodipine, methotrexate, 5-aminosalicylic acid, amitriptyline, amlodipine, amoxicillin, anastrozole, atenolol, atorvastatin, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, celetoxib, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytarabine, dapiprazole, desogestrel, desonide, dihydralazine, diltiazem, ergot alkaloids, dimenhydrinate, dimethyl sulfoxide, dimethicone, dipyridamole, domperidone and domperidone derivatives, donepzil, dopamine, doxazosin, doxorubicin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, esomeprazole, estrogen and estrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitor, fluconazole, fludarabine, flunarizine, fluorouracil, fluoxetine, flurbiprofen, ibuprofen, flutamide, fluvastatin, follitropin, formoterol, fosfomicin, furosemide, fusidic acid, galantamine, gallopamil, ganciclovir, gemfibrozil, gentamicin, ginkgo, St John's wort, glibenclamide, urea derivatives as oral antidiabetics, glucagon, glucosamine and glucosamine derivatives, glutathione, glycerol and glycerol derivatives, hypothalamus hormones, goserelin, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixen, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline, and adrenaline derivatives, norfloxacin, novaminsulfone, noscapine, nystatin, ofloxacin, olanzapine, olsalazine, omeprazole, omoconazole, ondansetron, orlistat, oseltamivir, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenyloin, pimozide, pindolol, piperazine, piracetam, pirenzepine, piribedil, piroxicam, pramipexol, pravastatin, prazosin, procaine, promazine, propiverine, propranolol, propyphenazone, prostaglandins, protionamide, proxyphylline, quetiapine, quinapril, quinaprilate, ramipril, ranitidine, reproterol, reserpine, ribavirin, rifampicin, risperidone, ritonavir, ropinirol, rosiglitazone, roxatidine, roxithromycin, ruscogenin, rutoside and rutoside derivatives, sabadilla, salbutamol, salmeterol, scopolamine, selegiline, sertaconazole, sertindole, sertraline, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiam, sumatriptan, suxamethonium chloride, tacrine, tacrolimus, taliolol, tamoxifen, taurolidine, tazarotene, tegaserod, temazepam, teniposide, tenoxicam, terazosin, terbinafine, terbutaline, terfenadine, terlipressin, tertatolol, tetracyclines, tetryzoline, theobromine, theophylline, butizine, thiamazole, phenothiazines, thiotepa, tiagabine, tiapride, propionic acid derivatives, ticlopidine, timolol, timidazole, tioconazole, tioguanine, tioxolone, tiropramide, tizanidine, tolazoline, tolbutamide, tolcapone, tolnaftate, tolperisone, topotecan, torasemide, antiestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutin, tulobuterol, tyramine, tyrothricin, urapidil, ursodeoxycholic acid, chenodeoxycholic acid, valaciclovir, valdecoxib, valproic acid, vancomycin, vecuronium chloride, venlafaxine, verapamil, vidarabine, vigabatrine, viloxazine, vinblastine, vincamine, vincristine, vindesine, vinorelbine, vinpocetine, viquidil, warfarin, xantinol nicotinate, xipamide, zafirlukast, zalcitabine, zanamivir, zidovudine, zolmitriptan, zolpidem, zopiclone, zotepine and the like.

The active ingredients can if desired also be used in the form of their pharmaceutically acceptable salts or derivatives, and in the case of chiral active ingredients it is possible to employ both optically active isomers and racemates or mixtures of diastereoisomers. The compositions of the invention can if desired also comprise two or more active pharmaceutical ingredients.

The dispersions of the invention are preferably employed for coating tablets, extrudates, minitablets, capsules, soft capsules, granules, pellets, micropellets, microcapsules, crystals. Coated granules, pellets, micropellets, microcapsules, crystals can be mixed with suitable excipients and compressed to tablet which rapidly disintegrate in water and release the coated fine shaped articles again. It is possible in this way to produce so-called MUPS forms, multiple unit particulate systems. These are tablets which disintegrate after intake and which release subunits coated with a coating composition of the invention. Of particular importance in this connection are so-called oral dispersibles, i.e tablets which disintegrate within a short time in the mouth and release taste-masked small shaped articles.

In a specific variant, the dispersions of the invention are used for granulating active ingredients, if appropriate with appropriate excipients, and the granules are then compressed to tablets.

The dispersions of the invention can also be used to produce transdermal active ingredient patches or sprays.

It is likewise suitable to incorporate agglomerates in polyethylene glycol or lipids to produce suppositories or vaginal pharmaceutical forms.

Active ingredient classes and substances which may often elicit a bitter taste and which can advantageously be formulated with the coating compositions and binders of the invention are for example:
analgesics and antirheumatics such as paracetamol, diclofenac, aceclofenac, ibuprofen, ketoprofen, flubiprofen, acetylsalicylic acid, levacetylmethadol and oxycodone;
psychoactive drugs such as promethazine, donepezil, modafinil, nefazodone, reboxetin, sertindole and sertraline;
antibiotics such as erythromycin, roxithromycin, clarithromycin, grepafloxacin, ciprofloxacin, levofloxacin, sparfloxacin, trovafloxacin and nevirapin;
beta blockers such as propranolol, metoprolol, bisoprolol and nebivolol;
antidiabetics such as metformin, miglitol and repaglinid;
$H_1$ antihistamines such as diphenhydramine, fexofenadine and mizolastine;
$H_2$ antihistamines such as cimetidine, famotidine, roxatidine, nizatidine, ticlopidine, cetirizine and ranitidine;
vitamins such as thiamine nitrate, and quinidine sulfate, amyloprilose HCl, pseudoephedrine HCl, sildenafil, topiramate, granisetron, rebamipide, quinine HCl, etc.

The outstanding suitability for taste masking results from the insolubility of the polymers of the invention at pH values above 6 and the rapid solubility at pH values below 6. This means that correspondingly coated forms are stable for a very long time in saliva (pH 7.2), and there is no contact of the bitter medicinal substance with the oral mucosa, but the active ingredient is released very rapidly in the stomach at pH values from 1 to 5. Dissolution is moreover so rapid that there is no difference in the onset of action compared with an uncoated form. Film coatings of a polymer of the invention generally dissolve within 5 min in gastric juice, whereas they are stable for more than 2 hours in phosphate buffer of pH 7.2. Surprisingly, the film coatings also dissolve relatively rapidly in media with pH values of 4.5, so that the dosage forms produced therefrom display a rapid effect even in patients with anacidity or patients who are treated with antacids.

The coating compositions of the invention exhibit a low permeability for water vapor and oxygen and thus make it possible to formulate and stabilize medicinal substances which are particularly sensitive to water vapor and sensitive to oxygen, such as, for example, acetylsalicylic acid, enalapril, cortisone acetate, omeprazole, carotenoids. The coating has protective characteristics in these cases.

The coating compositions of the invention can additionally be used to separate incompatible active ingredients or excipients in dosage forms by enveloping one or more ingredients and thus preventing mutual contact.

The unexpectedly excellent technical use properties of the film coatings of the invention are made possible by an excellent homogeneous film formation of the polymer dispersion, a low tackiness of the films and the good flexibility or elasticity of the coatings, so that the film coating does not crack even if the tablet or pellet core swells. It is particularly surprising in this connection that high flexibility is combined with extremely low tackiness, because polymers are normally either rigid, i.e. of low flexibility and not tacky, or soft, i.e. flexible but tacky.

The polymer dispersions have low viscosity, so that high solids concentration in the spray suspension and an extremely short spraying process can be achieved. The solids concentrations in the spray suspension are normally from 10 to 60% by weight, preferably 20 to 50% by weight and in particular 25 to 40% by weight. The concentration based on solid amino group-containing polymer employed according to the invention is normally in a range from 5 to 50% by weight, preferably from 10 to 40% by weight and especially from 20 to 35% by weight. The low viscosities ensure very fine and uniform atomization in the spray nozzle, very good spreading on the tablet or pellet surface and rapid and homogeneous film formation. Incorporation of colorants and pigments takes place in the usual way, but is extremely simple and rapid and solvent-free. The simple handling results from the fact that the amino group-containing polymer dispersions employed according to the invention stabilize the pigments in the spray suspension. A suspension ready for spraying can be prepared within about 10 min in this way.

The formulation base of pharmaceutical compositions of the invention preferably comprises pharmaceutically acceptable excipients. Pharmaceutically acceptable excipients are those known to be usable in the area of pharmacy, food technology and adjacent sectors, in particular the excipients listed in relevant pharmacopeias (e.g. DAB, Ph. Eur., BP, USP, JP), and others whose properties do not stand in the way of physiological use.

Suitable excipients may be: lubricants, wetting agents, emulsifying and suspending agents, preservatives, antioxidants, anti-irritants, chelating agents, emulsion stabilizers, film formers, gel formers, odor-masking agents, resins, hydrocolloids, solvents, solubilizers, neutralizers, permeation promoters, pigments, colorants, stabilizers, disintegrants, dessicants, opacifiers, thickeners, waxes, plasticizers, flavors, sweeteners, excipients to reduce permeation etc. An arrangement concerning this is based on specialist knowledge as described for example in Fiedler, H. P. Lexikon der Hilfsstoffe für Pharmazie, Kosmetik and angrenzende Gebiete, 4$^{th}$ edition, Aulendorf: ECV-Editio-Cantor-Verlag, 1996.

Examples of particularly suitable plasticizers are: triethyl citrate, tributyl citrate, triacetin, acetyl triethyl citrate, Labrasol, glycofurol, polypropylene glycol 400.

The permeability of the film coatings can be reduced further by incorporating inorganic solids (pigments such as, for example, talc, kaolin, titanium dioxide) or lipophilic organic solids such as fats, waxes, glycerides, fatty acids such as, for example, stearic acid, fatty alcohols such as, for example, stearyl alcohol.

The pharmaceutical compositions of the invention can be produced by mixing or diluting the active ingredients with suitable excipients. Excipients may be solid or semisolid materials which may serve as vehicle, carrier or medium for the active ingredient. Admixture of further excipients if desired takes place in a manner known to the skilled worker.

It is also possible in the same way to produce veterinary medical dosage forms, in particular rumen-stable forms, and dosage forms with vitamins, carotenoids, trace elements, nutraceuticals, amino acids and dietary supplements. The latter may also be regarded as food products or supplements.

A further aspect of the invention is the use of an aqueous polymer dispersion Pd) as defined above for producing membranes, in cosmetics, in crop protection, for seed coating, in food products, in animal nutrition, as adhesive raw material, for paper manufacture, as binder or auxiliary for leather and textile, as microbicidal surface coating, in the nonwoven sector, in detergents and cleaners, for producing paints, in the building sector.

A further aspect of the invention is the use of an aqueous polymer dispersion Pd) as defined above as or in coating composition(s) for cosmetics, food products, animal nutrition, the textile, paper, printing, leather and adhesives industries.

The invention is explained in more detail by means of the following, non-restrictive examples.

EXAMPLE 1

Initial Charge:
481.75 kg of deionized water
5.59 kg of $C_{16}/C_{18}$-alkyl polyglycol ethers with about 20 ethylene oxide units, Pharma grade, 10% strength aqueous solution,
4.58 kg of sodiumlaurylsulfate GMP, 15% strength aqueous solution
Addition 1:
14.60 kg of deionized water
0.38 kg of sodium persulfate
Feed 1:
248.52 kg of deionized water
86.43 kg of $C_{16}$-/$C_{18}$-alkyl polyglycol ethers with about 20 ethylene oxide units, Pharma grade, 10% strength aqueous solution
71.38 kg of sodiumlaurylsulfate GMP, 15% strength aqueous solution
Feed 2:
172.00 kg of diethylaminoethyl methacrylate
258.00 kg of methyl methacrylate
Feed 3:
153.09 kg of deionized water
3.92 kg of sodium persulfate It is ensured by suitable technical measures (flushing with acetone and/or blowing dry) that the feed vessel (feed 2) is substantially free of water. Addition 1 and feed 3 are freshly made up directly, i.e. 1 hour, before the start of the polymerization (solid sodium persulfate dissolved in deionized water). The dynamic mixer (Megatron MT 3-61, Kinematica AG) is charged with water before the start of the test.

The polymerization reactor (vessel volume about 2050 l) and all lines coming into contact with the polymer dispersion are flushed with a 3% strength aqueous sodium hydroxide solution before the start of the test. The polymerization reactor is then charged with the initial charge. Before starting the reaction, the initial charge is evacuated, gassed once with 5 bar of nitrogen, again evacuated and brought to atmospheric pressure with nitrogen. The initial charge is then heated to the reaction temperature of 75° C. while stirring. When an internal temperature of 70° C. is reached, addition 1 is added over the course of two minutes.

Feeds 1 and 2 are metered into the reactor via the dynamic mixer (revolutions set at 5000 rpm), feed 3 is metered into the reactor via a static mixer which is located in the stretch of line between dynamic mixer and polymerization reactor.

Feed 1 is started directly before feeds 2 and 3. Addition of feed 1 takes place over the course of 1.75 hours, of feed 2 over the course of 1.50 hours, and of feed 3 over the course of 3.75 hours.

After feed 3 is complete, after-polymerization takes place at 75° C. while stirring for 2 hours. The reaction mixture is then cooled to room temperature and the solids content and pH are determined. The pH during the polymerization (more accurately: during the addition of the monomers) was always higher than 8.0 in Example 1 and the following Examples 2 to 6. The K values were determined on 1% strength solutions in NMP for all examples.

| Characteristics of the dispersion | Unit | Measurement or assessment |
|---|---|---|
| Solids content | (wt. %) | 32.7 |
| pH | | 9.0 |

The dispersion then undergoes ultrafiltration and the following characteristics are determined:

| Characteristics of the dispersion | Unit | Measurement or assessment |
|---|---|---|
| Solids content | (wt. %) | 30.5 |
| Viscosity | (mPas) | 6 |
| pH | | 9.2 |
| Light transmission | (%) | 86 |
| K value | | 50 |
| Average particle size (determined using an AU) | (nm) | 100 |
| Methanol | (ppm) | 20 |
| Methacrylic acid | (ppm) | 60 |
| N,N-Diethylethanolamine | (ppm) | 280 |
| Storage stability (18 months) | | excellent, no sediment |

AU = analytical ultracentrifuge

EXAMPLE 2

The procedure is as in Example 1, but only 2.2 kg of sodium persulfate are employed in feed 3, and 0.4 kg of ethylhexyl thioglycolate are included in feed 2.

| Characteristics of the dispersion | Unit | Measurement or assessment |
|---|---|---|
| Solids content | (wt. %) | 31.9 |
| pH | | 9.1 |

The dispersion then undergoes ultrafiltration and the following characteristics are determined:

| Characteristics of the dispersion | Unit | Measurement or assessment |
|---|---|---|
| Solids content | (wt. %) | 30 |
| Viscosity | (mPas) | 6 |
| pH | | 9.2 |
| Light transmission | (%) | 87 |
| K value | | 52 |
| Average particle size (determined using an AU) | (nm) | 105 |
| Methanol | (ppm) | 18 |
| Methacrylic acid | (ppm) | 48 |
| N,N-Diethylethanolamine | (ppm) | 240 |
| Storage stability (after 18 months) | | excellent, minimal sediment |

Example 3

The procedure is as in Example 1, but 193.5 kg of diethylaminoethyl methacrylate and 236.5 kg of methyl methacrylate are employed in feed 2.

| Characteristics of the dispersion | Unit | Measurement or assessment |
|---|---|---|
| Solids content | (wt. %) | 30.3 |
| pH | | 9.0 |

The dispersion then undergoes ultrafiltration and the following characteristics are determined:

| Characteristics of the dispersion | Unit | Measurement or assessment |
|---|---|---|
| Solids content | (wt. %) | 30 |
| Viscosity | (mPas) | 5 |
| pH | | 9.2 |
| Light transmission | (%) | 89 |
| K value | | 50 |
| Average particle size (determined using an AU) | (nm) | 110 |
| Methanol | (ppm) | 22 |
| Methacrylic acid | (ppm) | 65 |
| N,N-Diethylethanolamine | (ppm) | 210 |
| Storage stability (after 18 months) | | excellent, minimal sediment |

EXAMPLE 4

Initial Charge:
378.24 kg of deionized water
5.59 kg of $C_{16}$-/$C_{18}$-alkyl polyglycol ethers with about 20 ethylene oxide units, Pharma grade, 10% strength aqueous solution,
4.58 kg of sodiumlaurylsulfate GMP, 15% strength aqueous solution
Addition 1:
14.60 kg of deionized water
0.38 kg of sodium persulfate
Feed 1:
352.03 kg of deionized water
86.43 kg of $C_{16}$-/$C_{18}$-alkyl polyglycol ethers with about 20 ethylene oxide units, Pharma grade, 10% strength aqueous solution
71.38 kg of sodiumlaurylsulfate GMP, 15% strength aqueous solution
Feed 2:
172.00 kg of diethylaminoethyl methacrylate
258.00 kg of methyl methacrylate Feed 3:
153.09 kg of deionized water
3.92 kg of sodium persulfate The polymerization reactor (vessel volume about 2050 l) and all lines coming into contact with the polymer dispersion are flushed with a 3% strength aqueous sodium hydroxide solution before the start of the test. The polymerization reactor is then charged with the initial charge.

Before starting the reaction, the initial charge is evacuated, gassed once with 5 bar of nitrogen, again evacuated and brought to atmospheric pressure with nitrogen. The initial charge is then heated to the reaction temperature of 75° C. while stirring. When an internal temperature of 70° C. is reached, addition 1 is added over the course of two minutes.

Feeds 1 and 2 are metered into the reactor via the dynamic mixer (revolutions set at 5000 rpm), feed 3 is metered into the reactor via a static mixer which is located in the stretch of line between dynamic mixer and polymerization reactor.

Feed 1 is started directly before feeds 2 and 3. Addition of feed 1 takes place over the course of 1.75 hours, of feed 2 over the course of 1.50 hours, and of feed 3 over the course of 3.75 hours.

After feed 3 is complete, after-polymerization takes place at 75° C. while stirring for 2 hours. The reaction mixture is then cooled to room temperature and the solids content and pH are determined.

| Characteristics of the dispersion | Unit | Measurement or assessment |
|---|---|---|
| Solids content | (wt. %) | 31.7 |
| pH | | 9.0 |

The dispersion then undergoes ultrafiltration and the following characteristics are determined:

| Characteristics of the dispersion | Unit | Measurement or assessment |
|---|---|---|
| Solids content | (wt. %) | 30 |
| Viscosity | (mPas) | 6 |
| pH | | 9.2 |
| Light transmission | (%) | 85 |
| K value | | 50.5 |
| Average particle size (determined using an AU) | (nm) | 105 |
| Methanol | (ppm) | 20 |
| Methacrylic acid | (ppm) | 40 |
| N,N-Diethylethanolamine | (ppm) | 210 |
| Storage stability (18 months) | | excellent, no sediment |

EXAMPLE 5

The procedure is as in Example 4, but potassium persulfate is employed instead of sodium persulfate in addition 1 and in feed 3.

| Characteristics of the dispersion | Unit | Measurement or assessment |
|---|---|---|
| Solids content | (wt. %) | 30.8 |
| pH | | 9.1 |

The dispersion then undergoes ultrafiltration and the following characteristics are determined:

| Characteristics of the dispersion | Unit | Measurement or assessment |
|---|---|---|
| Solids content | (wt. %) | 30 |
| Viscosity | (mPas) | 6 |
| pH | | 9.2 |
| Light transmission | (%) | 89 |
| K value | | 51 |
| Average particle size (determined using an AU) | (nm) | 110 |
| Methanol | (ppm) | 15 |
| Methacrylic acid | (ppm) | 55 |
| N,N-Diethylethanolamine | (ppm) | 190 |
| Storage stability (after 18 months) | | excellent, minimal sediment |

EXAMPLE 6

The procedure is as in Example 4, but ammonium persulfate is employed instead of sodium persulfate in addition 1 and in feed 3, and the pH is adjusted to pH 9 in each case with aqueous NaOH.

| Characteristics of the dispersion | Unit | Measurement or assessment |
|---|---|---|
| Solids content | (wt. %) | 30.7 |
| pH | | 8.9 |

The dispersion then undergoes ultrafiltration and the following characteristics are determined:

| Characteristics of the dispersion | Unit | Measurement or assessment |
|---|---|---|
| Solids content | (wt. %) | 30 |
| Viscosity | (mPas) | 7 |
| pH | | 9.1 |
| Light transmission | (%) | 85 |
| K value | | 51 |
| Average particle size (determined using an AU) | (nm) | 115 |
| Methanol | (ppm) | 25 |
| Methacrylic acid | (ppm) | 50 |
| N,N-Diethylethanolamine | (ppm) | 210 |
| Storage stability (after 18 months) | | excellent, minimal sediment |

In a variant of the examples indicated above it is, of course, also possible to prepare dispersions with a solids content differing from 30% by weight. For this purpose it is possible for example for deionized water to be added
a) to the initial charge and/or
b) to feed 1 and/or
c) to feed 3
(aiming at a lower solids content) or to be removed (aiming at a higher solids content).

In another embodiment it is possible for example to put water from the initial charge into feed 1 and/or feed 3, in which case the solids content is then not changed. The redistribution may, however, also be effected in such a way that the water removed from the initial charge and/or feed 1 and/or feed 3 is put wholly or partly into a new feed ("feed 4"), in which case feed 4 can then be added to the polymerization in parallel, to the polymerization with a time lag or after the polymerization, continuously or all at once. This may serve for example to adapt the formulation to the sizes of vessels available, e.g. to avoid overfilling or replenishment of feed 1.

It may, of course, be advantageous for the emulsifier distribution to the initial charge and feed 1 disclosed in the examples to be varied in such a way that anionic and/or nonionic emulsifier from the initial charge is put into feed 1 (or vice versa). It is, of course, also possible for anionic and/or nonionic emulsifier from the initial charge and/or feed 1 to be put into an additional feed 4 (cf. above). With all these measures it is preferred for the total amount of emulsifier to remain constant.

It may, of course, also be advantageous for feeds 1 and/or feed 2 and/or feed 3 not to be metered in at a constant rate, but to be introduced at a non-constant rate. For example, the initiator feed can be metered at a higher rate during the polymerization phase (i.e. during the addition of feed 2) than after completion of feed 2.

Example of Film Production

A 30% strength dispersion of diethylaminoethyl methacrylate-methyl methacrylate copolymer from Example 1 was mixed while stirring with 15% triethyl citrate, based on solids, and spread on a film applicator (Erichsen Coatmaster) and dried to a film at a plate temperature of 45° C. The film thickness was 100 μm.

The following properties were found:

| | |
|---|---|
| Elongation at break: | 93% |
| Tensile strength: | 9.8 N/mm$^2$ |
| Water vapor permeability to DIN 53122 at 93% r.h.: | 58 g/(m$^2$/d)/100 μm film |
| Dissolution time in 0.1N HCl | 2 min 50 s |
| Dissolution time in phosphate buffer of pH 6.8 | >120 min |
| Tackiness by the Hoessel method at 20° C./80% r.h. | 0.25 (with triacetin instead of triethyl citrate as plasticizer) |
| 30° C./75% r.h. | 0.25 (with triacetin instead of triethyl citrate as plasticizer) |

Method described in Cosmetics and Toiletries, 111(8), 73 et seq. (1996); scale from 0 (non-tacky) to 5 (tacky), r.h.=relative humidity

EXAMPLES OF COATING OF DOSAGE FORMS

Coating Example 1: Propranolol HCl 40 Mg Film-Coated Tablets

| Composition of the tablets | |
|---|---|
| Substance | Composition per tablet [mg] |
| Propranolol HCl | 40 |
| Ludipress | 97.5 |
| Avicel PH 105 | 97.5 |
| Kollidon VA 64 | 12.5 |
| Magnesium stearate | 2.5 |
| Total | 250 |

Format: 9 mm, coated tablet form

| Composition of the spray formulation | | |
|---|---|---|
| Substance | Proportion in the film [%] | Proportion in the suspension [%] |
| 30% aqueous dispersion from Example 2 | 67.83 | 45.22 |
| Triethyl citrate | 10.17 | 2.03 |

-continued

Composition of the spray formulation

| Substance | Proportion in the film [%] | Proportion in the suspension [%] |
|---|---|---|
| Iron oxide red | 2 | 0.4 |
| Talc | 20 | 4 |
| Water, demineralized | — | 48.35 |
| Total | 100 | 100 |

The triethyl citrate plasticizer was added to the polymer dispersion and stirring was continued. Talc and iron oxide red were slurried in water and homogenized using a high-shear mixer. The two phases were then mixed by adding the pigment suspension to the polymer dispersion.

Coating Parameters:

A Manesty "Accela Cota 24" horizontal drum coater was used for coating.

The following conditions were set or resulted from the settings:

| Spray nozzle | Schlick 937 with 1 mm liquid insert |
|---|---|
| Number of spray nozzles | 1 |
| Charge | 10 kg of propranolol HCl cores |
| Core bed-nozzle distance | 20 cm |
| Spraying pressure | 1.5 bar |
| Pattern air pressure | 0.5 bar |
| Inlet air temperature | 60° C. |
| Outlet air temperature | 36° C. |
| Drum speed | 15 rpm |
| Spraying rate | 40 g/min. |
| Spraying time | 55 min. |
| Drying | approx. 5 min. |
| Application rate | 6 mg/cm$^2$ |

Properties of the Film-Coated Tablets
Release
Paddle, 50 rpm, 37° C., 1000 ml

| | 0.08N HCl | Phosphate buffer pH 6.8 |
|---|---|---|
| after 45 min. | >90% | <5% |

Disintegration Time
Erweka type ZT 74 disintegration tester, 37° C., 800 ml

| 0.08N HCl (min:s) | Phosphate buffer pH 6.8 (min:s) |
|---|---|
| 4:30 | >45 min |

Coating Example 2: Enalapril 10 Mg Film-Coated Tablets

Composition of the tablets

| Substance | Composition per tablet [mg] |
|---|---|
| Enalapril | 10 |
| Avicel PH 102 | 120 |
| Di-Tab | 60 |
| Kollidon CL | 8 |
| Magnesium stearate | 2 |
| Total | 200 |

Format: 7 mm, coated tablet form

Composition of the spray formulation

| Substance | Proportion in the film [%] | Proportion in the suspension [%] |
|---|---|---|
| 30% aqueous dispersion from Example 3 | 62.4 | 41.60 |
| Tributyl citrate | 9.36 | 1.87 |
| Polyvinyl alcohol 5-88 | 6.24 | 1.25 |
| Water, demineralized | — | 30.88 |
| Titanium dioxide | 2.00 | 0.40 |
| Talc | 20.00 | 4.00 |
| Water, demineralized | — | 20.00 |
| Total | 100.00 | 100.00 |

The tributyl citrate plasticizer was added to the polymer dispersion and stirring was continued. Talc and titanium dioxide were slurried in water and homogenized using a high-shear mixer. Polyvinyl alcohol is heated to 85° C. in water and dissolved. The cooled solution is stirred into the polymer dispersion. The pigment suspension was then added with stirring.

Coating Parameters

A Manesty "Accela Cota 24" horizontal drum coater was used for coating.

The following conditions were set or resulted from the settings:

| Spray nozzle | Schlick 937 with 1 mm liquid insert |
|---|---|
| Number of spray nozzles | 1 |
| Charge | 12 kg of enalapril cores |
| Core bed-nozzle distance | 20 cm |
| Spraying pressure | 1.5 bar |
| Pattern air pressure | 0.5 bar |
| Inlet air temperature | 65° C. |
| Outlet air temperature | 38° C. |
| Drum speed | 15 rpm |
| Spraying rate | 45 g/min. |
| Spraying time | 50 min. |
| Drying | approx. 5 min. |
| Application rate | 5 mg/cm$^2$ |

Results
Release: Paddle, 50 rpm, 37° C., 1000 ml

| | 0.08N HCl | Phosphate buffer pH 6.8 |
|---|---|---|
| After 45 min. | >90% | <10% |

Disintegration time: Erweka type ZT 74 disintegration tester, 37° C.

| 0.08N HCl (min:s) | Phosphate buffer pH 6.8 (min:s) |
| --- | --- |
| 3:59 | >45 |

Stability: Storage at 30° C./70% r.h. for 1 year

| | Enalapril content (%) 0 months | Enalapril content (%) 12 months |
| --- | --- | --- |
| Core | 100.2 | 92.3 |
| Film-coated tablet | 100.7 | 100.1 |

Coating Example 3: Coated Ibuprofen Minipellets

Composition of the pellets

| Substance | Composition per pellet [%] |
| --- | --- |
| Ibuprofen | 100 |

Pellet size 200 to 400 μm

Composition of the spray formulation

| Substance | Proportion in film [%] | Proportion in suspension [%] |
| --- | --- | --- |
| 30% aqueous dispersion from Example 4 | 65.42 | 43.61 |
| Triacetin | 13.08 | 2.62 |
| Talc | 21.5 | 4.3 |
| Water, demineralized | — | 49.47 |
| Total | 100 | 100 |

The triacetin plasticizer was added to the polymer dispersion and left to stir. Talc was slurried in water and homogenized using a high-shear mixer. The two preparations were then mixed.

Coating Parameters

A "Glatt GPCG 3.1" fluidized bed granulator from Glatt was used for coating.

| Spray nozzle | 1 mm diameter |
| --- | --- |
| Number of spray nozzles | 1 |
| Charge | 2.5 kg of ibuprofen pellets 200-400 μm |
| Process | Bottom spray (Wurster) |
| Spraying pressure | 1.0 bar |
| Inlet air temperature | 60° C. |
| Outlet air temperature | 46° C. |
| Spraying rate | 12 g/min. |
| Spraying time | 4 h |
| Drying | approx. 5 min. |
| Application rate/weight gain | 20% |

Tabletting to MUPS Tablets

It is possible by mixing and compressing the coated pellets produced above with microcrystalline cellulose of type 102 to produce a tablet which disintegrates into pellets again on disintegration.

| Substance | Composition per tablet [mg] |
| --- | --- |
| Coated ibuprofen minipellets | 120 |
| Microcrystalline cellulose, type 102 | 258 |
| Kollidon CL | 20 |
| Magnesium stearate | 2 |
| Total | 400 |

Format: 11 mm, flat, bevelled

Tablet and Pellet Properties:
Release, pellets, paddle, 50 rpm, 37° C., 1000 ml, weight 250 mg

| | Acetate buffer pH 4.5 | Acetate buffer pH 6.8 |
| --- | --- | --- |
| After 45 min. | >90% | <10% |

Tablets:
Paddle, 50 rpm, 37° C., 1000 ml

| | Acetate buffer pH 4.5 | Acetate buffer pH 6.8 |
| --- | --- | --- |
| After 45 min. | >90% | <15% |

Tablet Disintegration:
Erweka type ZT 74 disintegration tester, 37° C.

| Acetate buffer pH 4.5 | Acetate buffer pH 6.8 |
| --- | --- |
| 2:29 | 2:45 |

Coating Example 4: Coated Caffeine Pellets

Composition of the pellets

| Substance | Composition per pellet [%] |
| --- | --- |
| Caffeine, fine powder | 20 |
| Avicel PH 101 (MCC) | 38.75 |
| Granulac 230 (Lactose) | 38.75 |
| Kollidon VA 64 | 2.5 |

Production by extrusion, pellet size 0.7-1.4 mm

Composition of the spray formulation

| Substance | Proportion in film [%] | Proportion in suspension [%] |
| --- | --- | --- |
| 30% aqueous dispersion from Example 5 | 62.61 | 41.74 |
| Acetyl triethyl citrate | 9.39 | 1.88 |
| Iron oxide yellow | 3 | 0.6 |
| Kaolin | 25 | 5 |
| Water, demineralized | — | 50.78 |
| Total | 100 | 100 |

The acetyl triethyl citrate plasticizer was added directly to the cationic polymer dispersion and left to stir. Talc and iron oxide yellow were slurried in water and homogenized using an Ultraturrax. The two phases were then mixed by adding the pigment suspension to the polymer dispersion.

Coating Parameters:

A "Glatt GPCG 3.1" fluidized bed granulator from Glatt was used for the coating.

The following conditions were set or resulted from the settings:

| Spray nozzle | 1 mm diameter |
|---|---|
| Number of spray nozzles | 1 |
| Charge | 2.5 kg of caffeine pellets 0.7-1.4 mm |
| Process | Top spray |
| Spraying pressure | 1.0 bar |
| Inlet air temperature | 60° C. |
| Outlet air temperature | 43° C. |
| Spraying rate | 14 g/min. |
| Spraying time | 135 min. |
| Drying | approx. 5 min. |
| Application rate/weight gain | 15% |

Release:
Paddle, 50 rpm, 37° C., 1000 ml, weight 300 mg

| | 0.08N HCl | Phosphate buffer pH 6.8 |
|---|---|---|
| After 45 min. | >95% | <10% |

Coating Example 5: Coated Quinine Sulfate Minipellets

| Composition of the pellets | |
|---|---|
| Substance | Composition per pellet [%] |
| Quinine sulfate * 2H$_2$O | 10 |
| Avicel PH 101 (MCC) | 46.75 |
| Granulac 230 (Lactose) | 40.75 |
| Kollidon VA 64 | 2.5 |

Pellet size 125-300 μm

| Composition of the spray formulation | | |
|---|---|---|
| Substance | Proportion in film [%] | Proportion in suspension [%] |
| 30% aqueous dispersion from Example 6 | 68.26 | 45.51 |
| Triacetin | 10.24 | 2.05 |
| Indigotine lake | 1.5 | 0.3 |
| Talc | 20 | 4 |
| Water, demineralized | — | 48.14 |
| Total | 100 | 100 |

The triacetin plasticizer was added directly to the polymer dispersion and left to stir. Talc and indigotine lake were slurried in water and homogenized using an Ultraturrax. The two preparations were then mixed by adding the pigment suspension to the polymer dispersion.

Coating Parameters:

A "Glatt GPCG 3.1" fluidized bed granulator from Glatt was used for the coating.

The following conditions were set or resulted from the settings:

| Spray nozzle | 1 mm diameter |
|---|---|
| Number of spray nozzles | 1 |
| Charge | 1.5 kg of quinine sulfate pellets 125-300 μm |
| Process | Bottom spray (Wurster) |
| Spraying pressure | 1.0 bar |
| Inlet air temperature | 60° C. |
| Outlet air temperature | 47° C. |
| Spraying rate | 10 g/min. |
| Spraying time | 225 min. |
| Drying | approx. 5 min. |
| Application rate/weight gain | 30% |

Release:
Paddle, 50 rpm, 37° C., 1000 ml, weight 1000 mg

| | 0.08N HCl | Phosphate buffer pH 6.8 |
|---|---|---|
| After 45 min. | >90% | <10% |

We claim:

1. An aqueous polymer dispersion Pd) which is soluble through reduction in the pH and comprises
   at least one polymer which comprises
   a) N,N-diethylaminoethyl methacrylate, and
   b) at least one compound capable of free radical polymerization and selected from esters of α,β-ethylenically unsaturated mono- and dicarboxylic acids with C$_1$-C$_8$-alkanols, wherein monomers a) and b) are the only monomers in the copolymer,
   at least one emulsifier selected from anionic and nonionic emulsifiers, and
   water.

2. The polymer dispersion according to claim 1, comprising a polymer which comprises
   43 to 47% by weight, based on the total weight of the monomers employed for the polymerization, of N,N-diethylaminoethyl methacrylate a), and
   53 to 57% by weight, based on the total weight of the monomers employed for the polymerization, of at least one compound b)
   as only monomers in the copolymer.

3. The polymer dispersion according to claim 1, which comprises N,N-diethylaminoethanol in an amount not exceeding 2500 ppm by weight.

4. The polymer dispersion according to claim 1, which comprises N,N-diethylaminoethanol in an amount not exceeding 500 ppm by weight, methacrylic acid in an amount not exceeding 50 ppm by weight and methanol in an amount not exceeding 50 ppm by weight.

5. The polymer dispersion according to claim 1, which comprises methacrylic acid in an amount not exceeding 100 ppm by weight.

6. The polymer dispersion according to claim 1, which comprises methanol in an amount not exceeding 500 ppm by weight.

7. A coating composition comprising an aqueous polymer dispersion Pd) as defined in claim 1, or a polymer composition obtainable therefrom by drying.

8. The coating composition according to claim 7, comprising in addition at least one further polymer component.

9. A pharmaceutical composition or food product comprising
   A) a polymer composition obtainable by drying and/or forming a film of a polymer dispersion as defined in claim 1, B) at least one pharmaceutically acceptable active ingredient or a dietary supplement, and
C) optionally at least one pharmaceutically acceptable excipient or auxiliary acceptable in the food products sector.

10. The pharmaceutical composition or food product in the form of an oral dosage form comprising a coating based on the aqueous polymer dispersion Pd) as claimed in claim 1.

11. The pharmaceutical composition or food product according to claim 1, which is in the form of coated tablets, pellets, microcapsules, granules or crystals.

12. A coating composition(s) for cosmetics, food products, veterinary medicaments, animal nutrition, seeds, and the textile, paper, printing, leather and adhesives industries which comprises the polymer as claimed in claim 1.

13. An aqueous polymer dispersion Pd) obtained by a process which comprises free-radical emulsion polymerizing a plurality of monomers in an aqueous medium at a pH of at least 8, said plurality of monomers consisting of
  a) N,N-diethylaminoethyl methacrylate, and
  b) a compound capable of free-radical polymerization selected from esters of α,β-ethylenically unsaturated mono and dicarboxylic acids with $C_1$-$C_8$ alkanols, and
  c) optionally a monomer c) selected from esters of α,β-ethylenically unsaturated mono and dicarboxylic acids with $C_9$-$C_{30}$-alkanols and $C_2$-$C_{30}$-alkanediols, amides of α,β-ethylenically unsaturated mono and dicarboxylic acids with $C_2$-$C_{30}$-amino alcohols which have a primary or secondary amino group, primary amides of α,β-ethylenically unsaturated monocarboxylic acids and theft N-alkyl and N,N diallyl derivatives, N-vinyl-lactams, open-chain N-vinylamide compounds, esters of vinyl alcohol and allyl alcohol with $C_1$-$C_{30}$-monocarboxylic acids, vinyl ethers, vinyl aromatic compounds, vinyl halides, vinylidene halides, $C_2$-$C_8$-monoolefins, unsaturated nitriles, nonaromatic hydrocarbons having at least two conjugated double bonds and mixtures thereof, and
  d) optionally a compound d) which is different from compound a) and has an α,β-ethylenically unsaturated double bond capable of free radical polymerization and at least one cationic group per molecule as copolymerized units.

\* \* \* \* \*